(12) United States Patent
Nakada et al.

(10) Patent No.: US 9,480,429 B2
(45) Date of Patent: Nov. 1, 2016

(54) STATE-OF-ATTENTION DETERMINATION APPARATUS

(75) Inventors: Toru Nakada, Kyoto (JP); Koji Morikawa, Kyoto (JP)

(73) Assignee: Panasonic Corporation, Osaka (JP)

(*) Notice: Subject to any disclaimer, the term of this patent is extended or adjusted under 35 U.S.C. 154(b) by 1085 days.

(21) Appl. No.: 13/207,547

(22) Filed: Aug. 11, 2011

(65) Prior Publication Data

US 2011/0295086 A1 Dec. 1, 2011

Related U.S. Application Data

(63) Continuation of application No. PCT/JP2010/006257, filed on Oct. 22, 2010.

(30) Foreign Application Priority Data

Nov. 9, 2009 (JP) ................................ 2009-256170

(51) Int. Cl.
*A61B 5/04* (2006.01)
*A61B 5/18* (2006.01)
(Continued)

(52) U.S. Cl.
CPC ............... *A61B 5/18* (2013.01); *A61B 5/0476* (2013.01); *A61B 5/0496* (2013.01); *G08G 1/166* (2013.01); *A61B 5/6803* (2013.01); *A61B 5/6814* (2013.01); *A61B 5/6816* (2013.01)

(58) Field of Classification Search
USPC ................................................ 600/544–545
See application file for complete search history.

(56) References Cited

U.S. PATENT DOCUMENTS 5,649,061 A 7/1997 Smyth
6,092,058 A * 7/2000 Smyth ............................ 706/10
(Continued)

FOREIGN PATENT DOCUMENTS

JP 7-108848 A 4/1995
JP 11-347008 A 12/1999
(Continued)

OTHER PUBLICATIONS

Supplementary European Search Report for Corresponding European Application No. 10828066.0 issued on Aug. 5, 2014.
(Continued)

*Primary Examiner* — Navin Natnithithadha
*Assistant Examiner* — Michael R Bloch
(74) *Attorney, Agent, or Firm* — Renner, Otto, Boisselle & Sklar, LLP

(57) ABSTRACT

The apparatus includes: a detection section for detecting a time period during which an operator is making preparations prior to beginning a driving operation; an adjustment section for adjusting a determination criterion for determining a state of attention of the operator during a driving operation, which calculates an eye fixation related potential of the electroencephalogram signal of the operator measured at least in the time period by using the measured oculomotor signal of the operator, and which adjusts the determination criterion based on the calculated eye fixation related potential; a determination section for calculating an eye fixation related potential from the electroencephalogram signal and the oculomotor signal of the operator measured after beginning the driving operation, which determines a state of attention of the operator during the driving operation based on the calculated eye fixation related potential and the adjusted determination criterion; and an output section for acting to call attention of the operator based on a result of determination.

13 Claims, 12 Drawing Sheets

(51) Int. Cl.
*A61B 5/0476* (2006.01)
*A61B 5/0496* (2006.01)
*G08G 1/16* (2006.01)
*A61B 5/00* (2006.01)

(56) References Cited

U.S. PATENT DOCUMENTS

| | | | |
|---|---|---|---|
| 7,431,120 | B2 | 10/2008 | Pollehn et al. |
| 2002/0183644 | A1 | 12/2002 | Levendowski et al. |
| 2007/0198189 | A1* | 8/2007 | Herbin ................. B60Q 1/0023 701/300 |
| 2009/0247895 | A1 | 10/2009 | Morikawa et al. |
| 2009/0268022 | A1* | 10/2009 | Omi .............................. 348/135 |
| 2009/0312665 | A1* | 12/2009 | Daimoto et al. .............. 600/544 |

FOREIGN PATENT DOCUMENTS

| | | |
|---|---|---|
| JP | 2002-272693 A | 9/2002 |
| JP | 2005-034620 A | 2/2005 |
| JP | 2007-38772 A | 2/2007 |
| JP | 2007-125184 A | 5/2007 |
| JP | 101049236 A | 10/2007 |
| JP | 2009-297129 A | 12/2009 |
| JP | 2010-057710 A | 3/2010 |

OTHER PUBLICATIONS

Chinese Search Report for Corresponding Chinese patent application No. 201080016580.3, dated Nov. 18, 2013.
Miyata et al., "New Physiopsychology 1", 1998, p. 262, Kitaoji Shobo with concise explanation.
Miyata et al., "New Physiopsychology 1", 1998, p. 256, Kitaoji Shobo with concise explanation.
"Jishoukanrenden I (ERP) Manyuaru-P300 Wo Chushinni (or Event-Related Potential (ERP) Manual-mainly concerning P300")", edited by Kimitaka Kaga et al., Shinohara Shuppan Shinsha, 1995 with concise explanation, p. 30.

* cited by examiner

LAMBDA RESPONSE AMPLITUDE VALUE
IN DRIVING OPERATION STANDBY STATE

EVALUATION VALUE (E)

| | AMPLITUDE VALUE (POTENTIAL) | EYEBALL ANGLE |
|---|---|---|
| HORIZONTAL DIRECTION | +50 μV | 5 DEGREES (RIGHT) |
| | -50 μV | 5 DEGREES (LEFT) |
| | ⋮ | ⋮ |
| VERTICAL DIRECTION | +30 μV | 5 DEGREES (ABOVE) |
| | -30 μV | 5 DEGREES (BELOW) |
| | ⋮ | ⋮ |

STATE-OF-ATTENTION DETERMINATION APPARATUS

This is a continuation of International Application No. PCT/JP2010/006257, with an international filing date of Oct. 22, 2010, which claims priority of Japanese Patent Application No. 2009-256170, filed on Nov. 9, 2009, the contents of which are hereby incorporated by reference.

BACKGROUND OF THE INVENTION

1. Field of the Invention

The present invention relates to a technique of assisting in safe driving by determining a state of attention (e.g., a state of being focused on driving or a state of being distracted) of an operator performing operation of a vehicle, such as driving an automobile, on the basis of an electroencephalogram.

2. Description of the Related Art

In recent years, in the development of safe driving assistance techniques, there are increasing needs for techniques of grasping the physical state or psychological state of a driver in real time and providing assistance which is adapted to the state of the driver. As a technique of objectively and quantitatively evaluating the state of a driver, attempts of quantifying the arousal level by using physiological indices, e.g., an electroencephalogram or nictitation, are being made. For example, Japanese Laid-Open Patent Publication No. 7-108848 discloses a technique of estimating the arousal level of a driver from a hypnagogic waveform pattern or an α wave component of the electroencephalogram.

However, the inventors consider it insufficient to employ the mere arousal level to define the state of a driver during driving. The reason is that the arousal level alone does not help define a state where attention is not directed to driving (a so-called state of distraction) although one is in wakeful state. Therefore, what is needed is not only the conventional dozing-off detection based on the arousal level, but also a technique of measuring and evaluating a specific state of attention with respect to driving (e.g., a "looking-aside of the conscious", which is the conscious being not focused on driving because of thinking about something else, or being absorbed in music or a conversation, for example).

In recent years, studies are undertaken to examine how much attention is being paid to a visual object by using an eye fixation related potential (EFRP) of the electroencephalogram. This method makes it possible to examine a state of attention to driving, including a looking-aside of the conscious. As used herein, an "eye fixation related potential" refers to a transient potential fluctuation in the brain which occurs in relationship with the end time of a rapid oculomotor movement (saccade), i.e., the start time of an eye fixation, while a person is working on a task or looking at things at liberty. Among the components of an eye fixation related potential, a positive component which appears more dominantly in the occiput than in the sinciput is especially referred to as a "lambda response". A lambda response is known to fluctuate with the degree of attention and concentration onto a visual object.

For example, in Japanese Laid-Open Patent Publication No. 2007-125184, in an environment where large and small saccades variously occur, the saccades are classified based on saccade size or patterns of line-of-sight movement, and an eye fixation related potential is calculated. Then, a degree of attention and concentration is evaluated from a specific component (e.g., the amplitude value of an eye fixation related potential component corresponding to a lambda response) of the calculated eye fixation related potential.

However, since the manner in which an electroencephalogram waveform appears is greatly affected by the individual difference of each driver, the conventional technique described in Japanese Laid-Open Patent Publication No. 2007-125184 cannot accurately determine a state of attention to driving.

This will be specifically described with reference to FIGS. 1A to 1C. FIGS. 1A to 1C show results of an experiment conducted by the inventors concerning the eye fixation related potential. FIG. 1A shows a waveform which is obtained as an arithmetic mean of the waveforms of all of test subjects measured at the occiput; FIG. 1B is a waveform which is obtained as an arithmetic mean of waveforms of test subject A taken through a plurality of measurements; and FIG. 1C is a waveform which is obtained as an arithmetic mean of waveforms of test subject B taken through a plurality of measurements. In each of the graphs of FIGS. 1A to 1C, the horizontal axis represents time (latency) based on the start time of an eye fixation defined as 0 milliseconds, in units of milliseconds. Moreover, the vertical axis represents potential (EERP amplitude) in units of µV, where downward reads positive. The solid line indicates the eye fixation related potential in a state of being focused on driving, whereas the dotted line indicates the eye fixation related potential in a state where attention is not paid to driving (i.e., a state of distraction).

According to the graph of FIG. 1A, the amplitude of a positive component (lambda response) which appears near about 100 milliseconds based on the eye fixation start time as a starting point is as large as 3.4 µV when focused on driving, and as small as 1.2 µV when distracted. It can be seen that the amplitude value of lambda response increases or decreases in accordance with the state of attention, as indicated by conventional knowledge. When determining the state of attention to driving of each test subject by using the amplitude value of a lambda response, it is desirable to set a certain threshold and determine a state of focused driving if the amplitude value of the lambda response is equal to or greater than the threshold, or determine a state of distraction if it is smaller than the threshold. In test subject A, the threshold may be set near 0.9 µV according to the graph of FIG. 1B. When an optimum threshold for determining a state of attention is determined based on a graph which is liable to individual differences, the value will greatly differ among test subjects. Thus, it will be seen that the state of attention to driving cannot be accurately determined without taking such individual differences into consideration.

One method of adjusting for such individual differences is previously performing an adjustment as to the determination criterion of each test subject, i.e., so-called calibration. For example, Japanese Laid-Open Patent Publication No. 2005-34620 proposes a method of adjusting for individual differences when using an electroencephalogram interface for distinguishing an option that a test subject wishes to select from among a plurality of options by utilizing an event-related potential of the electroencephalogram. In this method, one test subject is asked to previously perform about 100 runs of a task of selecting one option from among a plurality of options by using the electroencephalogram interface. Then, from the electroencephalogram data obtained from each task, the system learns characteristic features of the electroencephalograms of the respective individuals.

A similar method might also be possible for determining a state of attention to driving by using an electroencephalogram. However, the requirement of a complicated calibration task prior to driving is troublesome and is a lot of burden on the driver. Furthermore, it is practically impossible for actually driving to be conducted in a state of distraction on a public road for the sake of a previous calibration task, which makes it difficult to acquire a sufficient amount of data for learning in advance.

SUMMARY OF THE INVENTION

The present invention has been made in order to solve the above problems, and an objective thereof is, in an apparatus which determines a state of attention to driving by using an electroencephalogram that is susceptible to large individual differences among drivers, to accurately determine the state of attention of each driver, without asking the driver to previously perform any explicit calibration task.

A state-of-attention determination apparatus according to the present invention comprises: an electroencephalogram measurement section for measuring an electroencephalogram signal of an operator; an oculomotor measurement section for measuring an oculomotor signal indicating an oculomotor movement of the operator; a standby state detection section for detecting a time period during which the operator is making preparations prior to beginning a driving operation; a determination criterion adjustment section for adjusting a determination criterion for determining a state of attention while the operator is performing a driving operation, the determination criterion adjustment section calculating an eye fixation related potential of the electroencephalogram signal measured at least in the time period by using the oculomotor signal, and adjusting the determination criterion based on the calculated eye fixation related potential; a state-of-attention determination section for calculating an eye fixation related potential from the electroencephalogram signal and the oculomotor signal measured after the operator begins a driving operation, and determining a state of attention of the operator performing the driving operation based on the calculated eye fixation related potential and the adjusted determination criterion; and an output section for acting to call attention of the operator based on a result of determination.

The determination criterion adjustment section may adjust the determination criterion further based on a frequency power spectrum value of the electroencephalogram signal measured in the time period.

The state-of-attention determination section may determine the state of attention of the operator by comparing an amplitude value of a lambda response of the arithmetic-meaned eye fixation related potential against a determination threshold which is the determination criterion.

As the determination criterion, the determination criterion adjustment section may set a higher determination threshold as the lambda response amplitude value of the calculated eye fixation related potential increases, and set a lower determination threshold as the lambda response amplitude value decreases.

The determination criterion adjustment section may set a higher determination criterion as the power spectrum value of α waves contained in the electroencephalogram signal measured in the time period increases, and set a lower determination criterion as the power spectrum value of β waves contained in the electroencephalogram signal measured in the time period increases.

The state-of-attention determination apparatus may be used to determine the state of attention of the operator performing a driving operation of a vehicle and to call attention of the operator, and the standby state detection section may detect the time period by defining as a start time at least one of the following points in time: a start of an engine of the vehicle, a start of a setting manipulation for a car navigation system provided in the vehicle, release of a brake of the vehicle, and detection of a vehicle speed of the vehicle being equal to or less than a predetermined value.

The standby state detection section may detect the time period by defining as an end time at least one of the following points in time: completion of a setting manipulation for the car navigation system, detection of a vehicle speed of the vehicle being equal to or greater than a predetermined value, and a predetermined time after the start time.

Based on the oculomotor signal, the determination criterion adjustment section may detect as a start time of the eye fixation related potential a point in time at which the oculomotor movement of the operator has become smaller than a predetermined threshold.

As the amplitude value of the lambda response, the attention amount determination section may utilize a local maximum contained within 50±100 milliseconds of the arithmetic-meaned eye fixation related potential based on the eye fixation start time as a starting point.

Another state-of-attention determination apparatus according to the present invention comprises: a standby state detection section for detecting a time period during which an operator is making preparations prior to beginning a driving operation; a determination criterion adjustment section for adjusting a determination criterion for determining a state of attention while the operator is performing a driving operation, the determination criterion adjustment section using an oculomotor signal measured by an oculomotor measurement section for measuring an oculomotor signal indicating an oculomotor movement of the operator to calculate an eye fixation related potential of an electroencephalogram signal measured at least in the time period by an electroencephalogram measurement section for measuring an electroencephalogram signal of the operator, and adjusting the determination criterion based on the calculated eye fixation related potential; a state-of-attention determination section for calculating an eye fixation related potential from the electroencephalogram signal and the oculomotor signal measured after the operator begins a driving operation, and determining a state of attention of the operator performing the driving operation based on the calculated eye fixation related potential and the adjusted determination criterion; and an output section for acting to call attention of the operator based on a result of determination.

A state-of-attention determining method according to the present invention comprises: a step of measuring an electroencephalogram signal of an operator; a step of measuring an oculomotor signal indicating an oculomotor movement of the operator; a step of detecting a time period during which the operator is making preparations prior to beginning a driving operation; a step of adjusting a determination criterion for determining a state of attention while the operator is performing a driving operation, the step calculating an eye fixation related potential of the electroencephalogram signal measured at least in the time period by using the oculomotor signal, and adjusting the determination criterion based on the calculated eye fixation related potential; a step of calculating an eye fixation related potential from the electroencephalogram signal and the oculomotor signal measured after the operator begins a driving operation; a step of determining a state of attention of the operator performing the driving operation based on the calculated eye fixation related potential and the adjusted determination criterion; and a step of acting to call attention of the operator based on a result of determination.

A computer program according to the present invention is a computer program to be executed by a computer mounted in a state-of-attention determination apparatus, the computer program causing the computer to execute: a step of receiving data of an electroencephalogram signal of an operator; a step of receiving data of an oculomotor signal indicating an oculomotor movement of the operator; a step of detecting a time period during which the operator is making preparations prior to beginning a driving operation; a step of adjusting a determination criterion for determining a state of attention while the operator is performing a driving operation, the step calculating an eye fixation related potential of the electroencephalogram signal measured at least in the time period by using the oculomotor signal, and adjusting the determination criterion based on the calculated eye fixation related potential; a step of calculating an eye fixation related potential from the electroencephalogram signal and the oculomotor signal measured after the operator begins a driving operation; a step of determining a state of attention of the operator performing the driving operation based on the calculated eye fixation related potential and the adjusted determination criterion; and a step of acting to call attention of the operator based on a result of determination.

According to the present invention, without asking an operator to previously perform any explicit calibration task, it is possible to a maintain high accuracy in the determination of the state of attention (e.g., a state of being focused on driving or a state of being distracted) of each operator. Therefore, based on the result of determination, it is possible to provide appropriate assistance, e.g., attention calling, for each operator.

Other features, elements, processes, steps, characteristics and advantages of the present invention will become more apparent from the following detailed description of preferred embodiments of the present invention with reference to the attached drawings.

DETAILED DESCRIPTION OF PREFERRED EMBODIMENTS

Figure 1A:
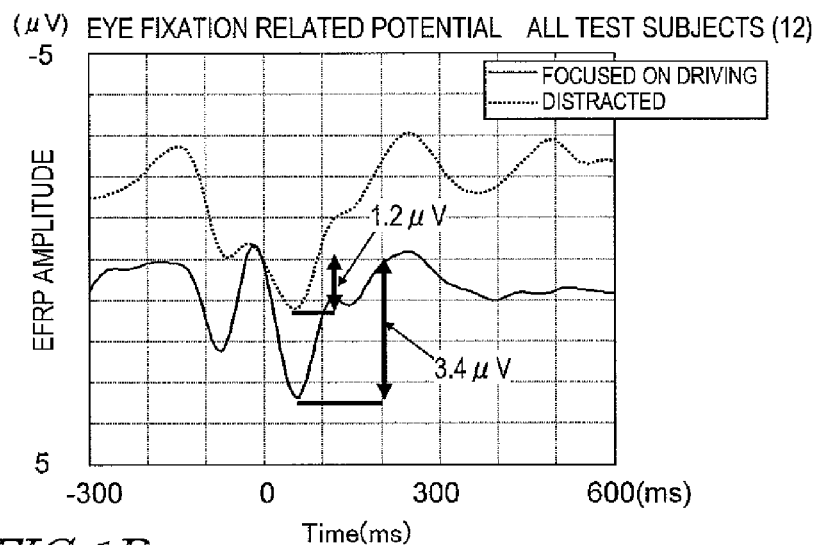
FIGS. 1A to 1C are diagrams showing results of an experiment conducted by the inventors concerning the eye fixation related potential.

Hereinafter, with reference to the attached drawings, an embodiment of a state-of-attention determination apparatus, method, and program according to the present invention will be described.

In the present embodiment, it is assumed that the state-of-attention determination apparatus is to be used in a situation where a driver performs a driving operation of a vehicle (automobile). Hereinafter, an experiment conducted by the inventors, and the findings which the inventors derived from the results of the experiment, will be described first.

From the experiment described below, the inventors have found that an optimum threshold for determining a state of attention to driving can be estimated for each driver based on the lambda response amplitude value of the eye fixation related potential in a driving operation standby state, and the power spectrum values of α waves, β waves, and θ waves among components of the electroencephalogram.

In the example of driving a vehicle such as an automobile, a "driving operation standby state" means a state of making preparations (e.g., engine start, manipulating a car navigation system, or releasing the parking brake) before beginning a travel (driving operation), or a state where the vehicle speed is less than 10 km/hour, which is generally considered as slow speed. As will be described later, the present invention does not need to be particularly limited to the operation of driving; therefore, the generic term "operation standby state" may be used. The "eye fixation related potential" and "lambda response" are as already described in the background art section.

Hereinafter, the details of the experiment conducted by the inventors will be described.

There were a total of 12 test subjects, including 7 males and 5 females, whose average age was 21.3±1.2 years. The inventors conducted an experiment by a dual task method, where each test subject was asked to concurrently perform two tasks.

The first task was a driving task. Each test subject was asked to perform a task of driving in a town course of about 6 minutes on a driving simulator (manufactured by MITSUBISHI PRECISION CO., LTD.; hereinafter abbreviated as a "DS"). The roads in the town course were set to a congestion level that allowed free traveling within the speed limit, and also preceding vehicles, oncoming vehicles, following vehicles, and pedestrians were provided. Following the instructions which were displayed on the screen of the car navigation system, each test subject traveled a predetermined route. However, the route was confirmed only via the test subject's own visual inspection of the screen, and no navigation via audio guidance was provided.

The second task was a cognitive load task. With a purpose of experimentally diverting the attention resource of the test subject from driving, a task called an n-Back test was performed. An "n-Back test" is a task where single-digit numbers in audio form are presented every 3 seconds, for example, and after the presentation, each number which was presented n steps earlier (e.g., 0 steps earlier, 2 steps earlier) is to be declared via voice utterance. This will be specifically described. For example, in the case where audio presentation of "3, 5, 9, 1, 6, . . . " is made at an interval of every 3 seconds and numbers which are 0 steps earlier (0-Back) are to be declared, the test subject is supposed to declare the presented numbers as they come, i.e., "3, 5, 9, 1, 6, . . . ". On the other hand, in the case where numbers which are 2 steps earlier (2-Back) are to be declared, the test subject is supposed to declare a number which is always 2 steps earlier, i.e., "-(no answer), -(no answer), 3, 5, 9, . . . ". As the value of n increases, more numerical values need to be temporarily memorized and updated by the test subject, which increases the cognitive load of the test subject. Therefore, this is believed to experimentally mock having thoughts during driving or having a conversation related to one's memory, and the like.

Next, the experimental conditions will be described. In this experiment, the electroencephalogram during driving was measured under two conditions as shown in Table 1. The first condition was a driving-focused condition. Under the driving-focused condition, DS operation (driving) and a 0-Back test are conducted concurrently. Since a 0-Back test does not present such a large cognitive load, this is considered to be a state of being able to focus on driving.

The second condition is a distracted condition. Under the distracted condition, DS operation (driving) and a 2-Back test are conducted concurrently. Since a 2-Back test presents a cognitive load, the test subject needs to allocate a lot of attention resource to performing this task, thus presumably causing a state of being distracted from driving.

TABLE 1

|  | first task | second task |
| --- | --- | --- |
| driving-focused condition | DS operation (driving) | 0-Back test |
| distracted condition | DS operation (driving) | 2-Back test |

Figure 2:
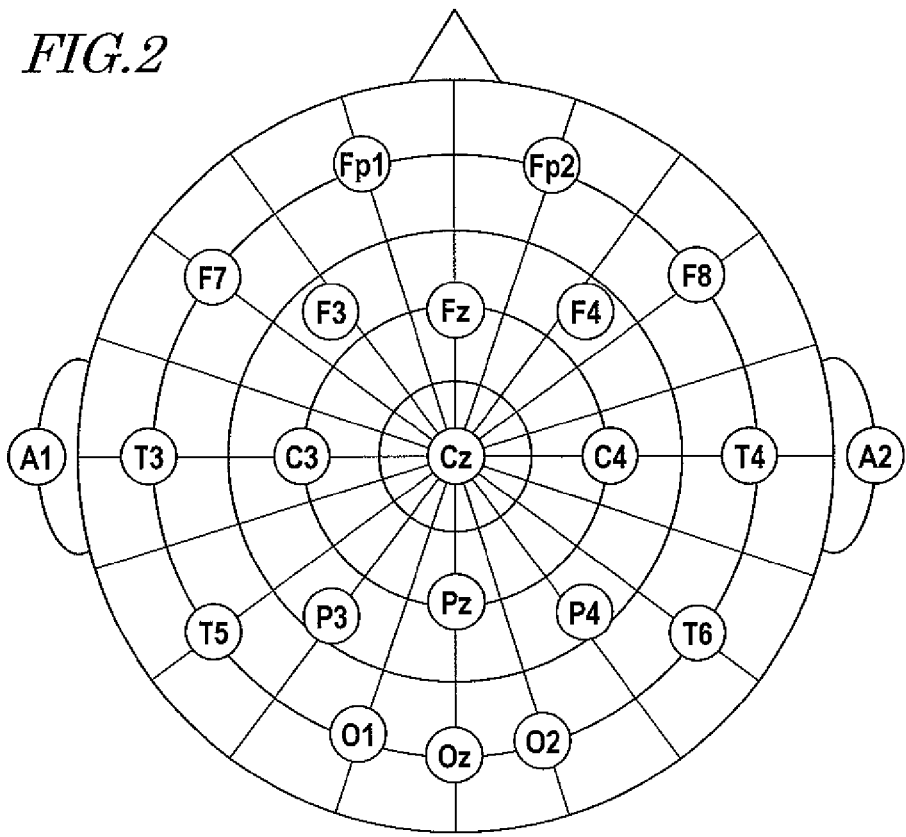
FIG. 2 is a diagram showing electrode positions in the International 10-20 system.

Moreover, each test subject was asked to wear an electroencephalograph (manufactured by TEAC Corporation; Polymate AP-1124). The electrode positioning of the electroencephalograph was as follows. A recording electrode was placed at Oz (occiput) in the International 10-20 system; reference electrodes were placed at A1 and A2 (average of both right and left earlobes); and a ground electrode was placed at the metopic. FIG. 2 shows electrode positions of the International 10-20 system. FIG. 2 shows the recording electrode Oz and the reference electrodes A1 and A2 at both of right and left earlobes.

Electroencephalogram data which was measured with a sampling frequency of 200 Hz and a time constant of 3 seconds was subjected to a bandpass filtering process of 1 to 15 Hz. Then, based on the saccade end time, i.e., the eye fixation start time as a starting point, electroencephalogram data from −300 milliseconds to 600 milliseconds was cut out, and subjected to a baseline correction with respect to a potential value at 0 milliseconds.

As described earlier, FIGS. 1A to 1C show arithmetic mean waveforms of eye fixation related potential (EFRP) after being subjected to the above process, where FIG. 1A shows an arithmetic mean waveform of all of 12 test subjects; FIG. 1B shows an arithmetic mean waveform of one test subject A; and FIG. 1C shows an arithmetic mean waveform of another test subject B. In each graph of FIGS. 1A to 1C, the solid line represents a waveform of the driving-focused condition, and the dotted line represents a waveform of the distracted condition. The horizontal axis represents time (latency) based on the start time of eye fixation as 0 milliseconds in units of milliseconds, and the vertical axis represents potential in units of $\mu V$.

Figure 1B:
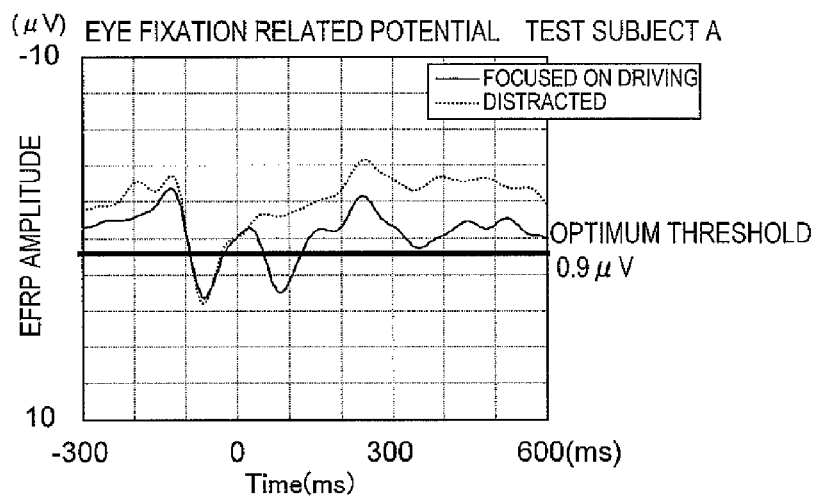
Figure 1C:
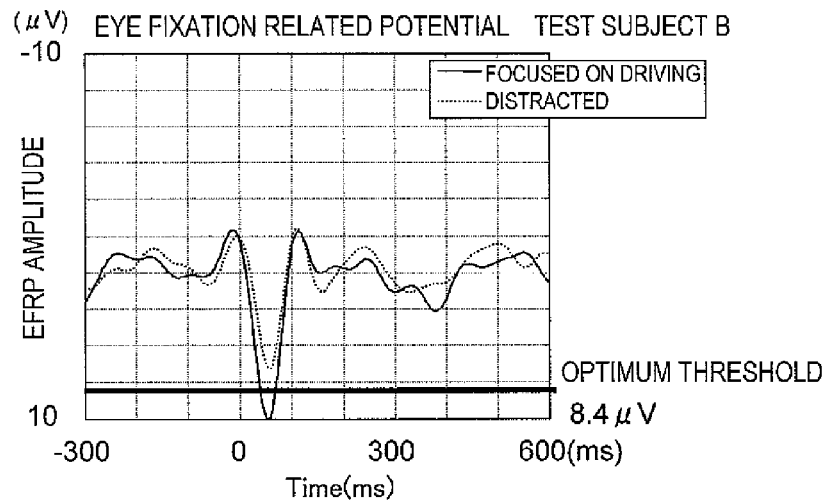

In the graph of FIG. 1A, the positive component appearing at a point in time of about 100 milliseconds (this component being a lambda response) is such that: the lambda response amplitude is as large as 3.4 $\mu V$ during driving (i.e., when the test subject is focused), and as small as 1.2 $\mu V$ when distracted. From this graph, it can be seen that the amplitude value of the lambda response increases or decreases in accordance with the state of attention.

Now, estimation of a state of attention as to whether each test subject's attention was focused on driving or was distracted will be discussed. In the present embodiment, an amplitude value of the lambda response and a threshold are employed, such that a state of focused driving is determined (estimated) when the amplitude value is greater than the threshold, or a state of distraction is determined (estimated) when the amplitude value is equal to or less than that.

Judging from the amplitude value of the lambda response, as for the test subject A of FIG. 1B, it is desirable to set a threshold near 0.9 $\mu V$, such that a state of focused driving is determined at this threshold or above, or a state of distraction is determined below this threshold. On the other hand, as for the test subject B of FIG. 1C, it is desirable to set a threshold near 8.4 $\mu V$ and determine a state of focused driving or a state of distraction. Thus, it can be seen that the optimum threshold for estimating a state of attention greatly differs from test subject to test subject, and that the state of attention to driving cannot be accurately determined without taking such individual differences into consideration.

Figure 3A:
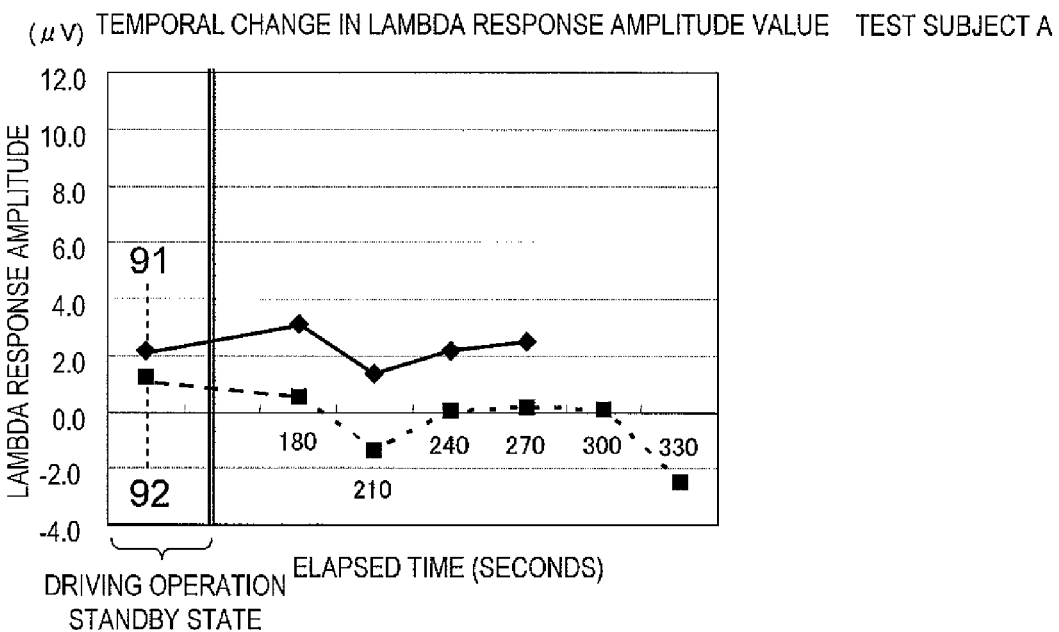
FIGS. 3A and 3B are diagrams showing temporal changes in lambda response amplitude values.
Figure 3B:
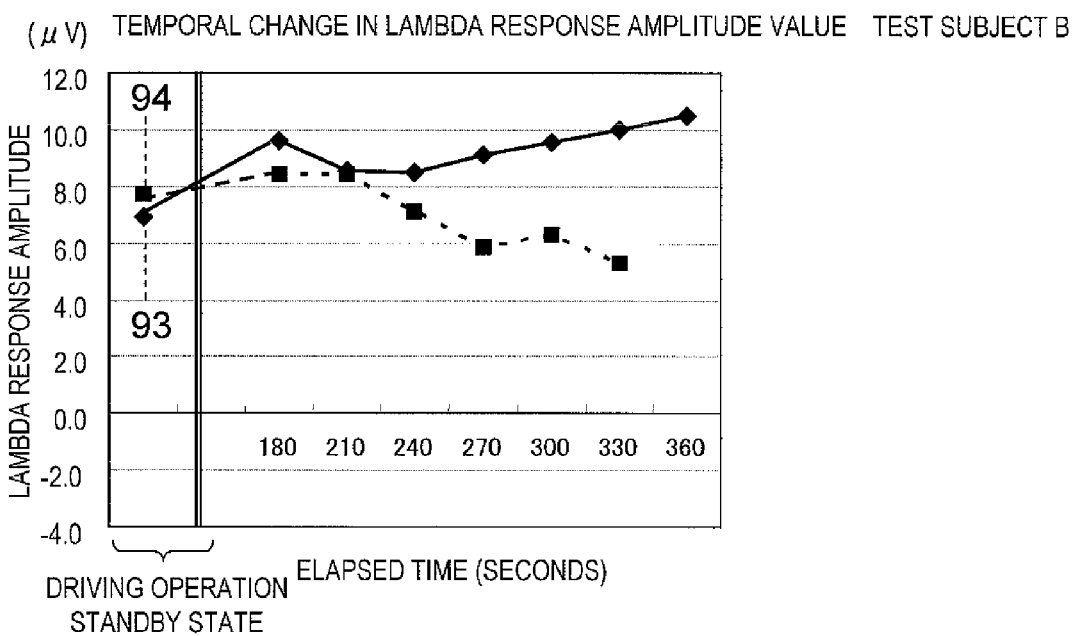

FIGS. 3A and 3B respectively show temporal changes in the lambda response amplitude values of test subjects A and B. The horizontal axis represents elapsed time in units of seconds. The vertical axis represents potential in units of $\mu V$, where upward reads positive. The solid line indicates the driving-focused condition, and the dotted line indicates the distracted condition.

First plots 91 to 94 at the left end of each graph of FIGS. 3A and 3B represent lambda response amplitude values calculated from EFRP arithmetic mean waveforms in a driving operation standby state. An exemplary time span of a "driving operation standby state" may be from the engine start until a predetermined time (45 seconds) has elapsed. The lambda response amplitude values of test subject A under the driving-focused condition and under the distracted condition shown in FIG. 3A are 2.2 μV (plot 91) and 1.2 μV (plot 92), respectively. The lambda response amplitude values of test subject B under the driving-focused condition and under the distracted condition shown in FIG. 3B are 6.9 μV (plot 93) and 7.8 μV (plot 94), respectively.

On the other hand, the second and later plots of each graph represent lambda response amplitude values calculated from EFRP arithmetic mean waveforms for the respective time periods for determination after the driving operation standby state, where a time span TW is set to 180 seconds and a time shift TS is set to 30 seconds.

According to the plots 91 to 94 in FIGS. 3A and 3B, the lambda response amplitude value in the driving operation standby state is not much influenced by differences in the state of attention, but significantly reflects the individual differences between test subject A and test subject B. It can also be seen that the lambda response amplitude value after the driving operation standby state reflects influences of the state of attention in addition to individual differences. Specifically, in the graphs of FIGS. 3A and 3B, the lambda response amplitude value has a level or increasing tendency when focused on driving, but has a decreasing tendency when distracted.

The inventors have made the following observation from such characteristics.

In a driving operation standby state, oculomotor movements associated with trivial tasks of confirmation will occur. For example, oculomotor movements occur in response to the engine start, manipulations of the car navigation system, releasing of the parking brake, watching of one's right and left before pulling out and during travel at a slow speed, and so on. Moreover, it is believed that a certain amount of attention resource is assigned to each such confirmation task, as necessary, in a driving operation standby state. The reason is that a manipulation of the car navigation system for setting a desired destination, and an operation of pulling a vehicle out of a relatively narrow place such as a parking lot while paying attention so that no bumping will occur at the front, rear, right, or left, constitute a sequence of tasks whose execution require a certain amount of attention, as compared to the relatively monotonous task of subsequent driving. Furthermore, each operation requires confirmation via visual inspection, and thus is considered to be a task that inevitably causes oculomotor movements.

Therefore, not only referring to a time range existing prior to travel or during travel at a slow speed, but a "driving operation standby state" may also be considered as a state where the aforementioned sequence of tasks is being actually executed. It is presumably for this reason that the lambda response amplitude value in a driving operation standby state is not much affected by differences in, the state of attention (experimental conditions) (i.e., the difference between the plots 91 and 92 or the difference between the plots 93 and 94 in FIG. 3B), but significantly reflects individual differences (i.e., the difference between the plots 91 and 92 in FIG. 3A and the plots 93 and 94 in FIG. 3B).

It would usually be preferable to make determination criterion adjustments for each driver (a so-called calibration) by utilizing the eye fixation related potential during actual driving, because the need to determine the state of attention of the driver during driving would make it naturally appropriate to acquire the eye fixation related potential during a driving time period, in which individual differences occur.

However, the inventors have recognized through experimentation that the states of attention of drivers have little variation and are rather constant, and that it is not so much during driving as in a driving operation standby state, which exists prior to driving (period of making preparations for driving), that the eye fixation related potential is likely to be affected by individual differences alone. Based on this finding, the time period of a driving operation standby state becomes an appropriate time zone for acquiring the eye fixation related potential of the driver, and it is preferable to make determination criterion adjustments for each driver (so-called calibration) by utilizing the eye fixation related potential during this driving operation standby state.

According to this approach, it is believed that an optimum threshold which takes each test subject's characteristics into consideration can be calculated by using a lambda response amplitude value in an operation standby state, which strongly reflects individual differences alone. An example of a simplest method may be to calculate an optimum threshold as follows.

$$Th = L \qquad \text{[Equation 1]}$$

Herein, L is a lambda response amplitude value in an operation standby state, and Th is an optimum determination threshold of each test subject.

Furthermore, specific calculation methods other than the above equation will be described in detail below.

Figure 4:
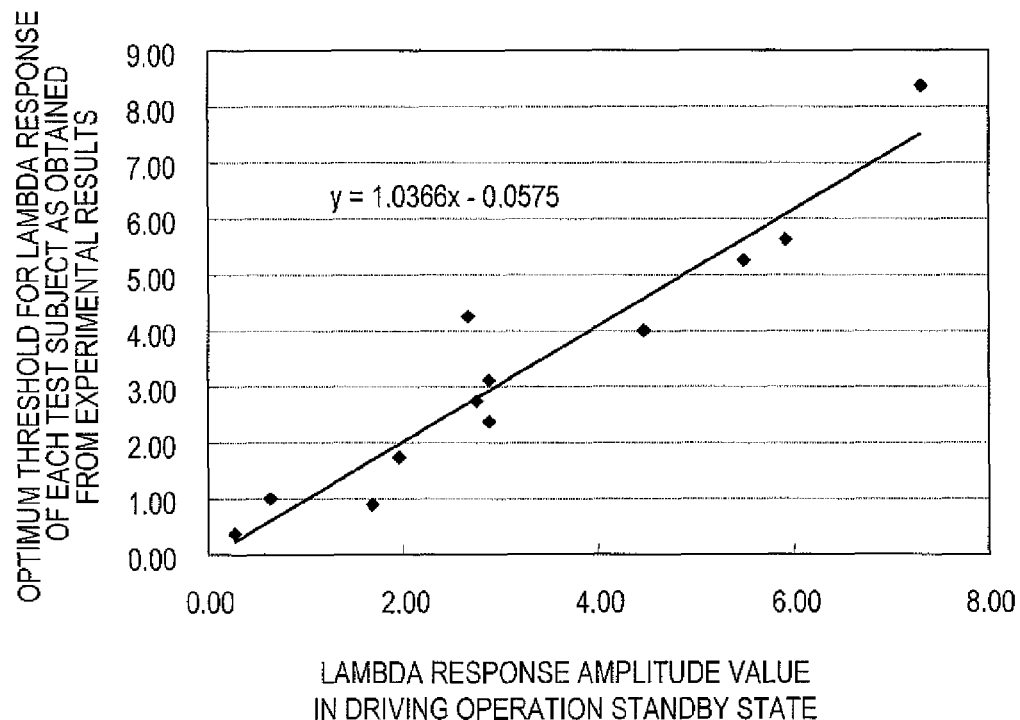
FIG. 4 is a diagram showing a relationship between the lambda response amplitude value and the optimum threshold in an operation standby state.

FIG. 4 shows a relationship between the lambda response amplitude value and the optimum threshold in an operation standby state. The horizontal axis represents the lambda response amplitude value (L) of each test subject in an operation standby state in units of μV, and the vertical axis represents the optimum determination threshold (Th) of each test subject in units of μV as obtained from the experimental result. As used herein, an "optimum determination threshold" is a value which is obtained from the results of conducting an experiment under both of the aforementioned driving-focused condition and distracted condition for each test subject. Specifically, when each lambda response amplitude value in the case where the time span TW=180 seconds and the time shift TS=30 seconds is to be categorized into either state of attention of being focused on driving or being distracted on the basis of a given certain threshold, the threshold that provides the highest distinction rate is defined as the "optimum determination threshold". As shown in FIGS. 1B and 1C, it is 0.9 μV for test subject A, and 8.4 μV for test subject B, for example.

As a result of subjecting the data plotted in FIG. 4 to a linear regression analysis, the optimum determination threshold (Th) can be approximated by the following equation.

$$Th = 1.0366 \cdot L - 0.0575 \qquad \text{[Equation 2]}$$

A correlation coefficient R in the approximate expression is 0.96, indicative of a very strong correlation relationship between the lambda response amplitude value and the optimum threshold in an operation standby state. A "correlation function" is a statistical index representing a correlation (degree of similarity) between two variables, and it is generally believed that a strong correlation exists when its absolute value is 0.7 or more. By utilizing this relationship, it becomes possible to estimate an optimum threshold from the lambda response amplitude value in an operation standby state.

As described above, it is possible to estimate a threshold based on the lambda response amplitude value alone. The inventors have further utilized the power spectrum values of α waves, β waves, and θ waves to determine a threshold, and made evaluations thereof.

Figure 5:
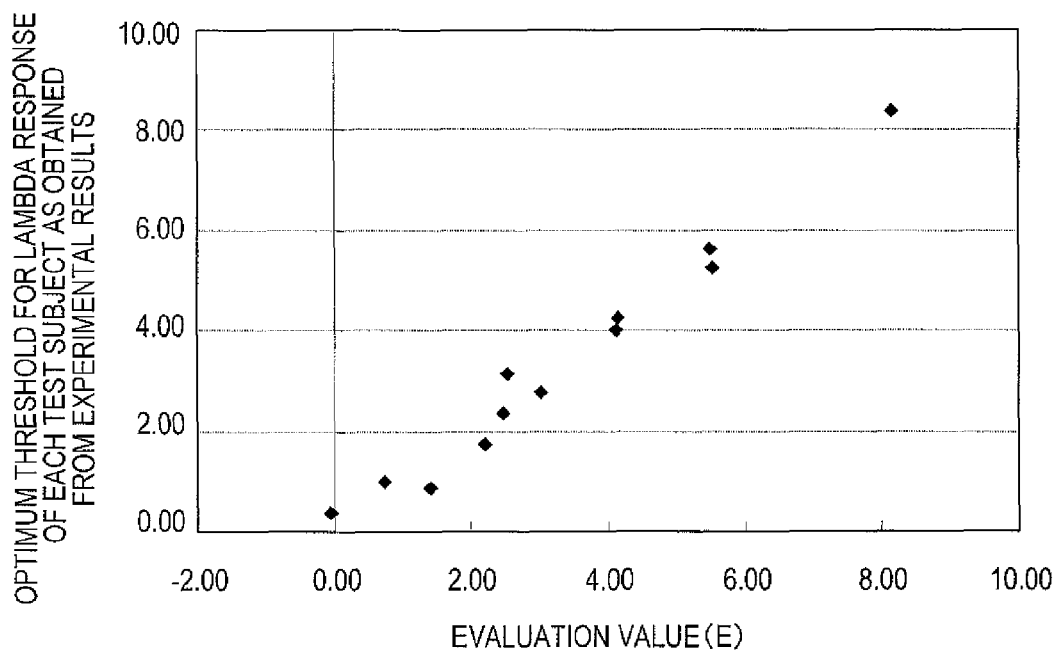
FIG. 5 is a diagram showing results of performing a multiple linear regression analysis, where the criterion variable is an optimum threshold of each test subject, and the explanatory variables are the lambda response amplitude value (L) and power spectrum values of α waves, β waves, and θ waves (α, β, θ) in an operation standby state.

FIG. 5 shows results of further performing a multiple linear regression analysis, where the criterion variable is an optimum threshold of each test subject, and the explanatory variables are the lambda response amplitude value (L) and power spectrum values of α waves, β waves, and θ waves (α, β, θ) in an operation standby state. The vertical axis represents the optimum threshold (Th) of each test subject in units of µV. The horizontal axis represents the evaluation value (E) as expressed by an approximate expression below. Between the evaluation value (E) and the optimum threshold, a linear relationship with a gradient of 1 and 0 intercept exists.

$$E = 0.9465 \cdot L + 1.0950 \cdot \alpha - 0.7410 \cdot \beta + 0.3406 \cdot \theta - 1.4438$$

$$Th = E \qquad \text{[Equation 3]}$$

The correlation coefficient R in the above approximate expression is 0.99, indicative of an even stronger correlation relationship than in the example of FIG. 4.

As described above, from the experiment of the inventors and its experimental results, it was found that the optimum threshold of each test subject can be estimated more accurately based only on the lambda response amplitude value in an operation standby state, or by employing the power spectrum values of α waves, β waves, and θ waves in addition to the lambda response amplitude value.

Note that, when vehicle operations are categorized into an operation of driving toward a destination (driving operation) and an operation of making preparations before beginning the driving operation, a "driving operation standby state" refers to the latter. The detection of a driving operation standby state may be made based on whether a predetermined time has elapsed or not since a given point in time, e.g., the engine start, and/or may be changed in accordance with the contents of the operational preparations. For example, if a shift lever operation or a stepping on the accelerator has been detected, it may be determined that the "driving operation standby state" has ended and a transition to a "driving operation state" has occurred.

Hereinafter, an embodiment of a state-of-attention determination apparatus according to the present invention, which was accomplished by the inventors based on the above findings, will be described. Although a situation of driving an automobile or the like will be illustrated as in the above description, this is exemplary.

Figure 6:
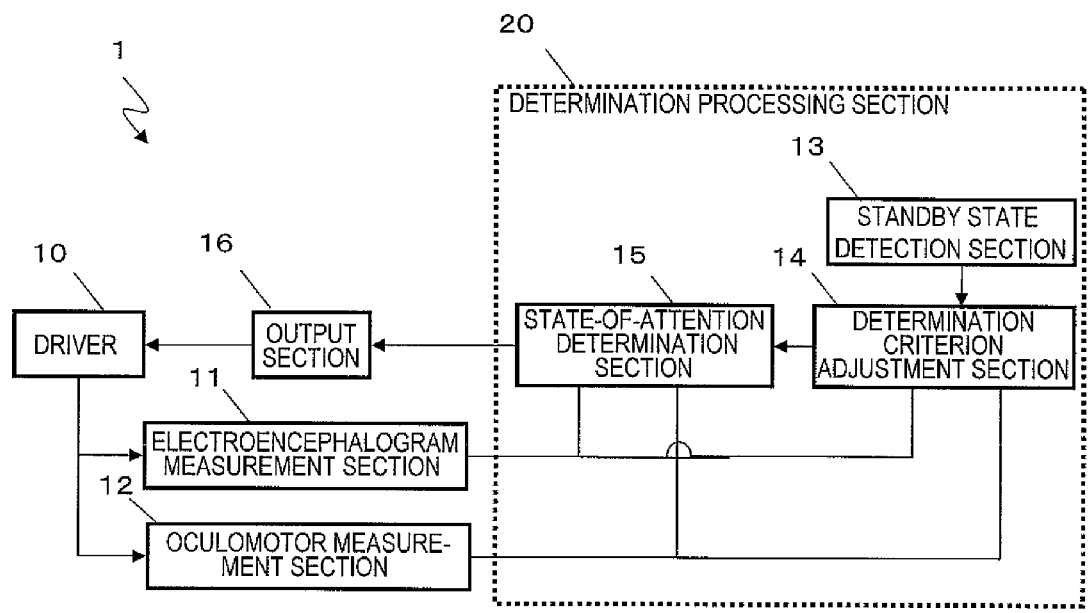
FIG. 6 is a block construction diagram of a state-of-attention determination apparatus 1 according to the present embodiment.

FIG. 6 shows a block construction diagram of a state-of-attention determination apparatus 1 according to the present embodiment. The state-of-attention determination apparatus 1 determines a state of attention to driving by utilizing an electroencephalogram signal of a driver 10, or more specifically, an eye fixation related potential which is a component of the electroencephalogram signal. As has been described earlier, a state of attention to driving is whether one's attention is focused on driving or distracted. Based on the state of attention, the state-of-attention determination apparatus 1 provides assistance of calling the attention of the operator. In order to precisely determine the state of attention, the determination criterion is adjusted for each driver in the state-of-attention determination apparatus 1. As a result, electroencephalograms which greatly differ from individual to individual can be precisely analyzed.

The state-of-attention determination apparatus 1 includes an electroencephalogram measurement section 11, an oculomotor measurement section 12, an output section 16, and a determination processing section 20. The determination processing section 20 includes a standby state detection section 13, a determination criterion adjustment section 14, and a state-of-attention determination section 15. Note that the driver 10 block is illustrated for ease of description.

Hereinafter, the respective constituent elements will be schematically described, and then specifically described in order.

The electroencephalogram measurement section 11 measures an electroencephalogram signal of the driver 10.

The oculomotor measurement section 12 measures oculomotor movements of the driver 10, and outputs an oculomotor signal indicating the oculomotor movements.

The standby state detection section 13 of the determination processing section 20 detects the time period of a driving operation standby state, i.e., a period over which a driving operation standby state continues. Based on the electroencephalogram data in the time period and the value of a specific component (described later) calculated from the oculomotor data, the determination criterion adjustment section 14 of the determination processing section 20 adjusts the determination criterion for determining a state of attention to driving. Moreover, by utilizing the oculomotor data measured by the oculomotor measurement section 12, the state-of-attention determination section 15 of the determination processing section 20 calculates an eye fixation related potential from the electroencephalogram data measured by the electroencephalogram measurement section 11, and determines a state of attention to driving based on the amplitude value of a specific component in the calculated eye fixation related potential and the determination criterion adjusted by the determination criterion adjustment section 14.

Based on the result of determination, the output section 16 provides assistance of calling the attention of the driver 10.

Hereinafter, each functional block will be described in detail.

The electroencephalogram measurement section 11 is an electroencephalograph which measures a potential by using electrodes which are worn on the head of the driver 10, and outputs an electroencephalogram signal by measuring potential changes therein. The inventors envisage that a wearable-type electroencephalograph will be used in future.

Figure 7:
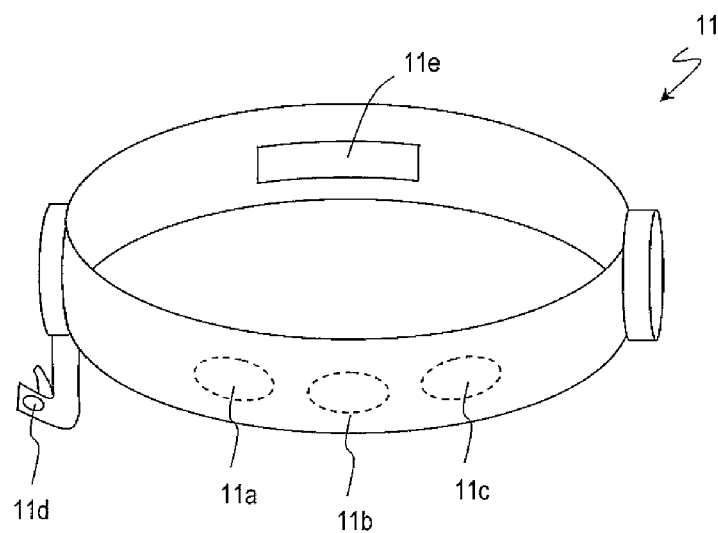
FIG. 7 is a diagram showing an exemplary construction of an electroencephalogram measurement section 11 implemented as a head-mount type electroencephalograph.

FIG. 7 shows an exemplary construction of the electroencephalogram measurement section 11 implemented as a head-mount type electroencephalograph. Electrodes 11a to 11e are disposed on the electroencephalogram measurement section 11 so that, when worn on the head of the driver 10, they come in contact with the head at predetermined positions. For example, the electrodes 11a and 11c are supposed to come in contact with electrode positions O1 and O2 at the occiput according to the International 10-20 system. Similarly, the electrode 11b comes in contact with the electrode position Oz at the occiput, the electrode 11d comes in contact with an earlobe A1, and the electrode 11e comes in contact with the metopic. According to previous literature (Yo MIYATA et al., "New Physiopsychology 1", 1998, p262 Kitaoji Shobo), the lambda component, which reflects perception or attention and appears near about 100 milliseconds based on the eye fixation start time as a starting point, is supposed to dominantly appear at the occiput.

However, measurement is also possible at Pz (parietal center) near the occiput, and a head-mount type electroencephalograph having an electrode disposed so as to come in contact with this position may be adopted. The electrode positions are to be determined based on reliability of signal measurements, wearing ease, and the like.

Moreover, there may be at least two electrodes. For example, potential measurement is possible with only the electrodes 11b and 11d corresponding to electrode positions Oz and A1.

By adopting such electrode positioning, the electroencephalogram measurement section 11 is able to measure an electroencephalogram of the driver 10. The measured electroencephalogram signal is sampled so as to be computer-processible, and is stored to a primary storage device (e.g. semiconductor memory) which is included in the electroencephalogram measurement section 11. Note that an auxiliary storage device (not shown) such as a hard disk drive may be provided in the state-of-attention determination apparatus 1, and the sampled electroencephalogram signals may be stored in that auxiliary storage device. For example, data spanning a predetermined fixed time is temporarily stored in the aforementioned primary storage device, and updated from time to time. Instead of temporarily, they may all be stored in the aforementioned auxiliary storage device.

In order to reduce the influence of noises on commercial power mixing into the electroencephalogram signal, it is preferable that the electroencephalogram signal measured by the electroencephalogram measurement section 11 is subjected to an advance low-pass filtering process. In the case where commercial power of e.g. 50 Hz or 60 Hz is to be used, the electroencephalogram signal may be subjected to a 30 Hz low-pass filtering process.

It is assumed that the driver 10 is wearing the aforementioned electroencephalograph in advance.

The oculomotor measurement section 12 measures oculomotor movements according to the EOG (Electrooculogram) method. The "EOG method" is a method of measuring oculomotor movements from potential changes in the electrodes that are disposed on the right and left and above and below an eyeball. The EOG method takes advantage of the nature of an eyeball's cornea that it is positively charged relative to the retina. The oculomotor measurement section 12 outputs a signal (oculomotor signal) indicating the oculomotor movements.

Figures 8, 9:
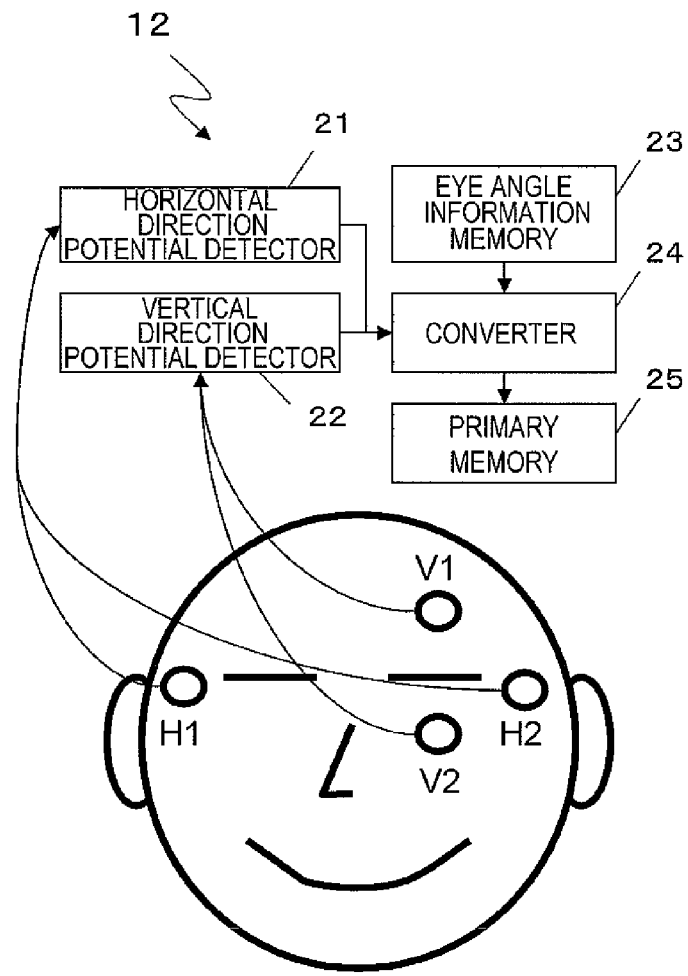
FIG. 8 is a diagram showing an exemplary hardware construction of an oculomotor measurement section 12 for measuring oculomotor movement by an EOG method.
FIG. 9 is a diagram showing an exemplary data structure of first eye angle information.

FIG. 8 shows an exemplary hardware construction for an oculomotor measurement section 12 which measures oculomotor movements by the EOG method and outputs an oculomotor signal indicating the oculomotor movements. The oculomotor measurement section 12 includes electrodes (H1, H2, and V1, V2), a horizontal direction potential detector 21, a vertical direction potential detector 22, an eye angle information memory 23, a converter 24, and a primary memory 25.

From a potential difference between the electrodes (H1, H2) worn at the right and left temples of the driver 10, the horizontal direction potential detector 21 detects a horizontal oculomotor signal indicating the motion of the eyeball along the horizontal direction. From a potential difference between the electrodes (V1, V2) worn above and below the eyeball, the vertical direction potential detector 22 detects a vertical oculomotor signal indicating the motion of the eyeball along the vertical direction. Note that a vector signal obtained by merging horizontal and vertical oculomotor signals may be used as a signal indicating the direction of oculomotor movement. In advance, the eye angle information memory 23 stores information (first eye angle information) indicating correspondence between the amplitude values of horizontal and vertical oculomotor signals and eyeball angles. Based on this eye angle information, the converter 24 measures an eyeball angle from each amplitude value. The primary memory 25 stores data spanning a predetermined fixed time, and updates it from time to time. The oculomotor measurement section 12 shown in FIG. 8 may be a head-mount type measuring instrument, similarly to the electroencephalograph.

FIG. 9 shows an exemplary data structure of the first eye angle information. In the first eye angle information, amplitude values (potential) along the horizontal direction and the vertical direction are associated with eyeball angles. For example, if the amplitude value (potential) changes by +50 μV along the horizontal direction and +30 μV along the vertical direction in 1 second, the eyeball angle can be identified to be 5 degrees (degrees) in the right direction and 5 degrees (degrees) in the upper direction. The angular velocity of the eyeball in this case can be calculated to be $(5^2+5^2)^{1/2} \approx 7.07$ degrees/second.

Alternatively, the oculomotor measurement section 12 may take measurements according to the corneal reflection method instead of the EOG method.

Figure 10:
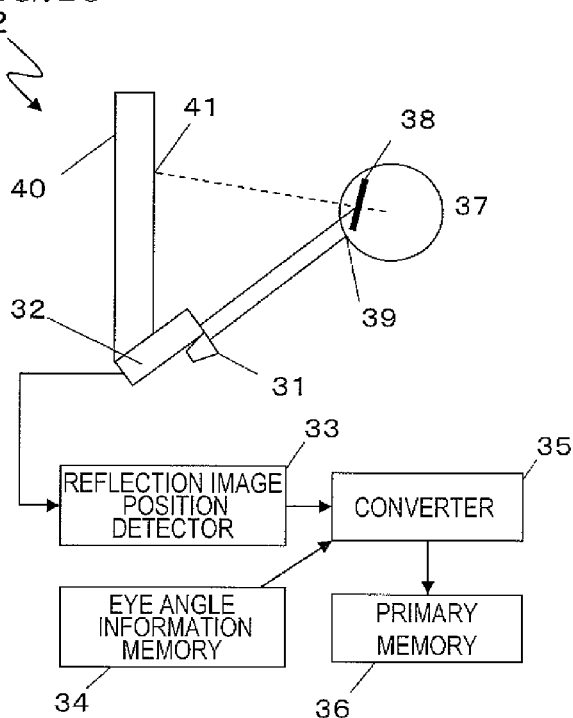
FIG. 10 is a diagram showing an exemplary hardware construction of an oculomotor measurement section 12 for measuring oculomotor movements by a corneal reflection method.

FIG. 10 shows an exemplary hardware construction for an oculomotor measurement section 12 which measures oculomotor movements by the corneal reflection method and outputs an oculomotor signal indicating the oculomotor movements. The "corneal reflection method" is a method where a near-infrared light source (point light source) irradiates an eyeball with near-infrared; a video of the eyeball is captured with a camera; and the position of a corneal reflection image of the light source at the pupil and the corneal surface is detected by using the captured video.

The oculomotor measurement section 12 includes a near-infrared light source 31, a CCD camera 32, a reflection image position detector 33, an eye angle information memory 34, a converter 35, and a primary memory 36.

The near-infrared light source 31 is a near-infrared point light source, which irradiates the eyeball 37 with near-infrared. The CCD camera 32 images the eyeball 37 irradiated with near-infrared. At this time, the test subject is gazing at an image or the like which is indicated on the display 40. The position to be gazed at is illustrated as a fixation point 41. Based on the capture video of the eyeball, the reflection image position detector 33 recognizes the pupil 38 and the corneal surface, and further detects the position of a reflection image (corneal reflection image 39) of the light source at the pupil 38 and the corneal surface. The eye angle information memory 34 stores the relationship (second eye angle information) between positions of the corneal reflection image 39 and angles of the eyeball 37 in advance. The data structure of the second eye angle information is similar to the data structure shown in FIG. 9, and its specific illustration is omitted.

Based on the eye angle information, the converter 35 measures an eyeball angle from the position of the reflection image. The primary memory 36 stores data spanning a predetermined fixed time, and updates it from time to time. The oculomotor measurement section 12 shown in FIG. 10 may be a head-mount type measuring instrument similarly to the electroencephalograph, or may be a stationary-type device that is disposed at the vehicle front (on the dashboard, behind the rear-view mirror, etc.).

Next, the specific construction of the determination processing section 20 (FIG. 6) will be described.

Figure 11:
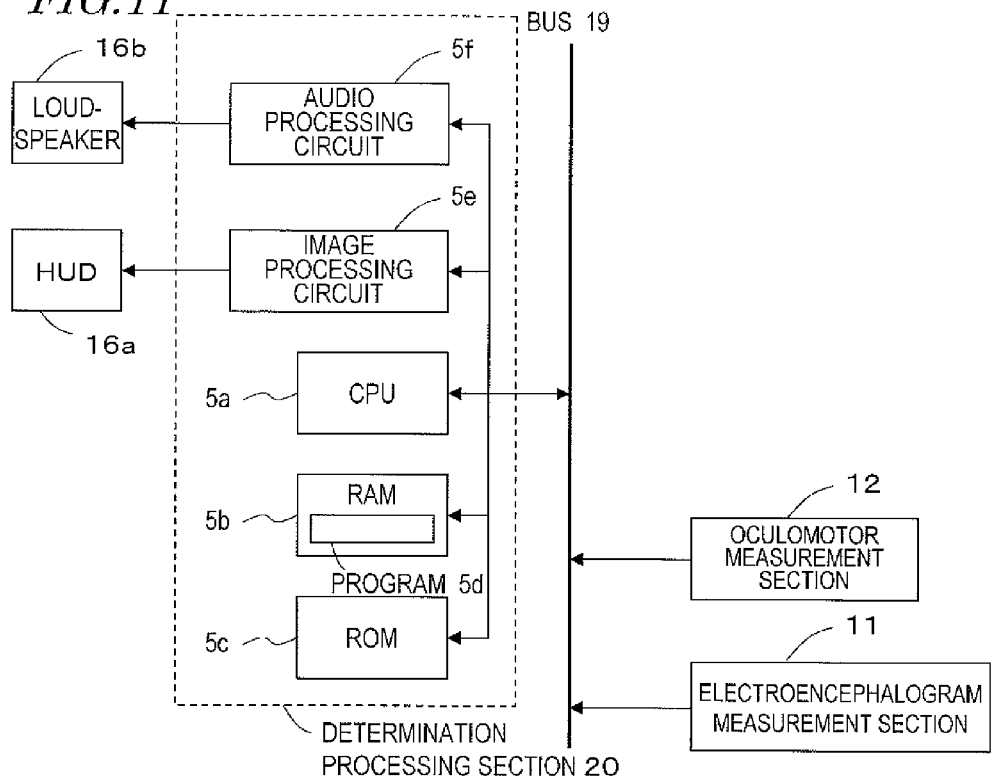
FIG. 11 is a diagram showing an exemplary hardware construction of a determination processing section 20.

FIG. 11 shows an exemplary hardware construction of the determination processing section 20. In order to show their relationship with the determination processing section 20, FIG. 11 also depicts the electroencephalogram measurement section 11 and the oculomotor measurement section 12 being connected to the determination processing section 20 via a bus 19.

The determination processing section 20 includes a CPU 5a, a RAM 5b, a ROM 5c, a program 5d, an image processing circuit 5e, and an audio processing circuit 5f.

The CPU 5a reads the computer program 5d which is stored in the ROM 5c onto the RAM 5b, where the computer program 5d is laid out and executed. By executing the computer program 5d, the CPU 5a functions as the standby state detection section 13, the determination criterion adjustment section 14, and the state-of-attention determination section 15, which have been described in connection with FIG. 6. The computer program 5d is a set of instructions to be executed by the CPU 5a. As the CPU 5a executes the computer program 5d, the CPU 5a or any constituent element receiving an instruction from the CPU 5a performs the processes defined in FIG. 12 and FIG. 14 described later. The ROM 5c may be a rewritable ROM (e.g., an EEPROM).

The determination processing section 20 further includes the image processing circuit 5e and the audio processing circuit 5f. In accordance with an instruction from the CPU 5a, the image processing circuit 5e generates data of an image to be displayed on a head-up display (HUD) 16a described later. In accordance with an instruction from the CPU 5a, the audio processing circuit 5f generates data of an audio to be output from a loudspeaker 16b in the car.

The aforementioned computer program may be distributed on the market in the form of a product recorded on a storage medium, such as a CD-ROM, or transmitted via telecommunication lines such as the Internet. Note that the determination processing section 20 can also be implemented in hardware, e.g., a DSP composed of a computer program incorporated in a semiconductor circuit.

Next, the respective operations (functions) when the CPU 5a of the determination processing section 20 executes the program 5d in order to operate as the standby state detection section 13, the determination criterion adjustment section 14, and the state-of-attention determination section 15 will be described.

The standby state detection section 13 detects the time period of a driving operation standby state.

Specific examples of start timings of the time period are the engine start, start of car navigation system manipulations, release of the parking brake, and the timing of detecting a state where the vehicle speed is less than 10 km/hour.

End timings of the time period may be, for example, the timing of detecting a state where the vehicle speed is 10 km/hour or more, completion of the setting of the car navigation system, and lapse of a predetermined time after the start timing (e.g., 45 seconds later).

The standby state detection section 13 detects at least one of the aforementioned start timings, and detects at least one of the aforementioned end timings. Furthermore, having detected both of the start and end timings marking the time period of a driving operation standby state, the standby state detection section 13 notifies the determination criterion adjustment section 14 of those results.

Based on the electroencephalogram data in the above time period and the value of a specific component calculated from the oculomotor data, specifically, based on the lambda response amplitude value of the eye fixation related potential, and power spectrum values e.g., $\alpha$ waves, $\beta$ waves, and $\theta$ waves, the determination criterion adjustment section 14 adjusts the determination criterion for determining a state of attention to driving. Now, a procedure of processing by the determination criterion adjustment section 14 will be described with reference to FIG. 12 and FIG. 13.

Figure 12:
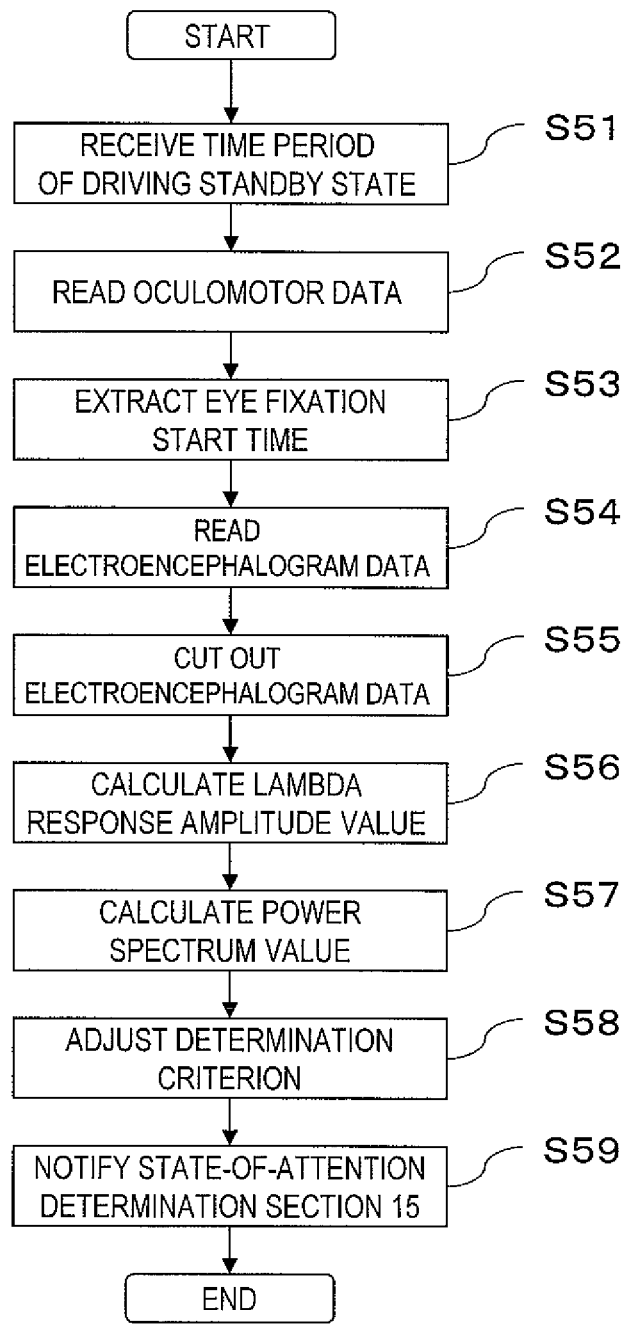
FIG. 12 is a flowchart showing a procedure of processing by a determination criterion adjustment section 14.
Figure 13:
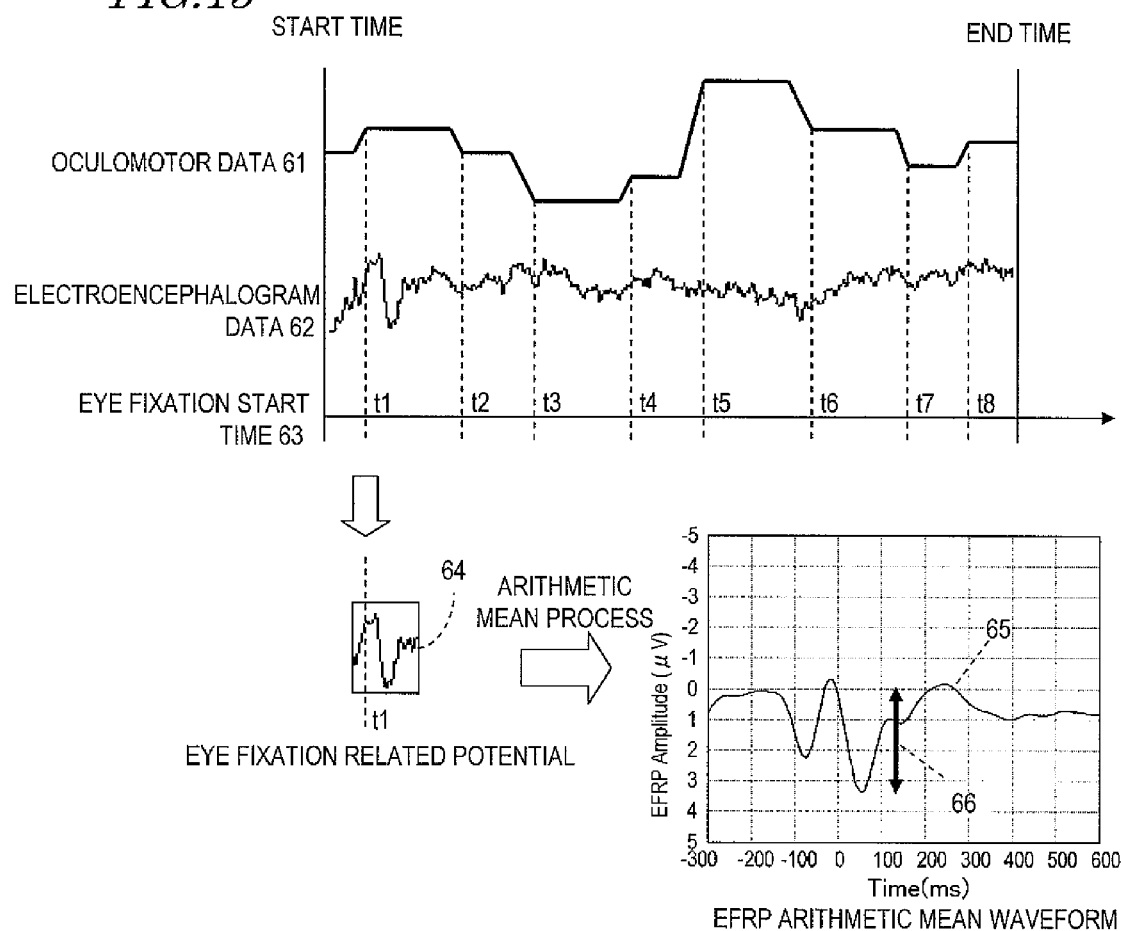
FIG. 13 is a diagram showing data of a waveform related to the processing by the determination criterion adjustment section 14.

FIG. 12 is a flowchart showing the procedure of processing by the determination criterion adjustment section 14, and FIG. 13 shows data of waveforms related to the processing by the determination criterion adjustment section 14.

At step S51 in FIG. 12, the determination criterion adjustment section 14 receives the start and end timings of the driving operation standby state as detected by the driving standby detection section 13.

At step S52, the determination criterion adjustment section 14 acquires from the oculomotor measurement section 12 the oculomotor data which was measured by the oculomotor measurement section 12 in the aforementioned time period. FIG. 13 shows an exemplary waveform of the oculomotor data 61 having been read.

At step S53, saccades in the aforementioned oculomotor data are detected, and the end time of each saccade detected, i.e., the eye fixation start time is extracted or identified.

According to previous literature (Yo MIYATA et al., "New Physiopsychology 1", 1998, p 256, Kitaoji Shobo), the time required for a saccade is usually 20 to 70 milliseconds, and the saccade velocity is 300 to 500 degrees (degrees)/second in terms of viewing angle. Therefore, any oculomotor movement such that the direction of movement of the eyeball continues to be the same for a predetermined time (e.g., 20 to 70 milliseconds) and that the average angular velocity during the predetermined time is equal to or greater than 300 degrees (degrees)/second can be detected as a saccade.

As a saccade detection method, a method may be employed where saccades in the horizontal and vertical directions are first detected, and thereafter any saccades in the horizontal and vertical directions which have overlapping time periods are combined into one saccade. A method may also be employed where vector data obtained by merging horizontal oculomotor data and vertical oculomotor data is calculated first, and saccade detection is performed based on the direction and size data of the vector data.

As an eye fixation start time, the determination criterion adjustment section 14 extracts each saccade end time that is detected. FIG. 13 shows examples of extracted eye fixation start times t1, t2, . . . , t8.

At step S54, the determination criterion adjustment section 14 acquires electroencephalogram data corresponding to the time period of a driving operation standby state received at step S51 from the electroencephalogram measurement section 11. FIG. 13 shows an exemplary waveform of the electroencephalogram data 62 that is read.

At step S55, in the electroencephalogram data having been read at step S54, the determination criterion adjustment section 14 cut outs electroencephalogram data from −300 milliseconds to 600 milliseconds based on the eye fixation start time extracted at step S53 as a starting point. FIG. 13 shows an exemplary waveform of the electroencephalogram data (eye fixation related potential) 64 that is cut out for every eye fixation start time.

At step S56, the determination criterion adjustment section 14 calculates an amplitude value of the lambda response from each electroencephalogram data having been cut out. Hereinafter, the procedure thereof will be described in detail.

First, the determination criterion adjustment section 14 subjects each electroencephalogram data having been cut out to a baseline correction so that the potential at the eye fixation start time (0 milliseconds) is 0 μV.

Next, the determination criterion adjustment section 14 performs an arithmetic mean process for all of the electroencephalogram data having been cut out. In the example of FIG. 13, electroencephalogram data corresponding to a total of 8 starting points, shown as the eye fixation start time 63 (t1, t2, . . . , t8), are subjected to an arithmetic mean process. FIG. 13 shows an exemplary waveform of the electroencephalogram data (eye fixation related potential) 65 after the arithmetic mean process.

Finally, in the arithmetic-meaned eye fixation related potential, the determination criterion adjustment section 14 measures an amplitude value of the lambda response, which is a positive component near about 100 milliseconds. FIG. 13 shows an example of the lambda response amplitude 66.

In the present specification, in order to define a component of the eye fixation related potential, a point in time after a predetermined time from an eye fixation start time is expressed as "about 100 ms", for example. This means that a range around a specific point in time of 100 ms may be included. Concerning the event-related potential, which is another component of an electroencephalogram signal similarly to the eye fixation related potential, "JISHOUKAN-RENDENI (ERP) MANYUARU—P300 WO CHUSHINNI (or "Event-Related Potential (ERP) Manual—mainly concerning P300"), edited by Kimitaka KAGA et al., Shinohara Shuppan Shinsha, 1995)" is known. According to Table 1 on p. 30 of this document, generally speaking, there are 30 ms to 50 ms of differences (shifts) in event-related potential waveform between individuals. Therefore, the terms "near about X ms" and "near X ms" mean that a breadth of 30 to 50 ms may exist before or after X ms (e.g., 100 ms±50 ms). It is considered that the eye fixation related potential also has differences (shifts) between individuals as does the event-related potential. Therefore, the present specification assumes that "near about 100 milliseconds" means e.g. a period of 50 milliseconds to 150 milliseconds also concerning the eye fixation related potential.

In the studies of the eye fixation related potential in general, an analysis is performed after taking an arithmetic mean of electroencephalogram data. As a result of this, any random action potentials of the brain that are not related to eye fixation are counteracted, whereby a component having a certain latency and polarity can be detected. However, the determination criterion adjustment section 14 of the present invention may measure a lambda response amplitude value from a non-cumulative electroencephalogram (i.e., a single piece of electroencephalogram data), without being limited to the aforementioned arithmetic mean process.

At step S57, the determination criterion adjustment section 14 calculates a power spectrum value for each frequency band of the electroencephalogram data having been read at step S54.

Generally speaking, a frequency component of the electroencephalogram that is 8 Hz or more but less than 13 Hz is referred to as $\alpha$ waves; a frequency component of 13 Hz or more is referred to as $\beta$ waves; and a frequency component of 4 Hz or more but less than 8 Hz is referred to as $\theta$ waves. Therefore, the determination criterion adjustment section 14 first determines frequency component data from the electroencephalogram data in chronological order through Fourier transform, and calculates a power spectrum of the electroencephalogram data as a product of the frequency component data and a complex conjugate thereof. By further calculating each of the aforementioned frequency components in the calculated power spectrum, the respective power spectrum values of $\alpha$ waves, $\beta$ waves, and $\theta$ waves are obtained.

At step S58, based on the lambda response amplitude value and the power spectrum values of $\alpha$ waves, $\beta$ waves, and $\theta$ waves calculated at step S56 and step S57, the determination criterion for determining a state of attention to driving is adjusted. More specifically, the determination criterion adjustment section 14 calculates an optimum threshold for each driver.

According to equations 1 to 3 above, it can be seen that the threshold (Th) to be estimated has a positive correlation with the lambda response amplitude value (L) in a driving operation standby state. In other words, the determination criterion adjustment section 14 may set a higher threshold (Th) as the lambda response amplitude value (L) in a driving operation standby state increases, and set a lower threshold (Th) as the lambda response amplitude value (L) in a driving operation standby state decreases.

Although the present embodiment illustrates an example where the lambda response amplitude value and power spectrum values are utilized, it is also possible to set a threshold based only on the lambda response amplitude value, as has been described in connection with equations 2 and 3 above.

In the case of utilizing power spectrum values, the determination criterion adjustment section 14 may set a higher threshold (Th) as the power spectrum value of $\alpha$ waves in a driving operation standby state increases, and set a lower threshold (Th) as the power spectrum value of $\beta$ waves in a driving operation standby state increases.

The inventors have found advantages of using power spectrum values as follows.

Generally speaking, it is supposed that $\beta$ waves appear in the electroencephalogram when psychological activities are taking place, whereas $\alpha$ waves appear in an absent-minded state. Therefore, when the $\alpha$ waves are large and the $\beta$ waves are small, i.e., in an absent-minded state, the threshold (Th) is increased according to equation 3 above.

The state-of-attention determination section 15 described later determines a "low" state of attention when the lambda response amplitude value during driving is smaller than the threshold (Th). Therefore, presumably, adjusting the threshold (Th) to be larger will make it possible to detect a state of being distracted without fail.

On the other hand, when the $\alpha$ waves are small and the $\beta$ waves are large, i.e., when psychological activities are taking place, the threshold (Th) becomes small according to equation 3. As a result, the possibility of wrongly determining the state of being focused on driving to be a "low" state of attention is presumably decreased.

The calculated threshold is used for determining the incessantly-changing state of attention to driving at the state-of-attention determination section 15 by using the lambda response amplitude value at each moment.

At step S59, the determination criterion adjustment section 14 notifies the state-of-attention determination section 15 of the resultant determination criterion adjusted at step S58.

Step S53 above is illustrated so that electroencephalogram data from −300 milliseconds to 600 milliseconds is cut out based on each extracted eye fixation start time as a starting point. However, the time span of the electroencephalogram data to be cut out is exemplary. For example, electroencephalogram data from 0 to 200 milliseconds may be cut out based on the eye fixation start time as a starting point. Alternatively, from the standpoint that it suffices if the lambda response is acquired, an arithmetic mean may be taken of the greatest value near 100 milliseconds based on each eye fixation start time as a starting point.

Next, the processing of the state-of-attention determination section 15 will be described.

From the electroencephalogram data and oculomotor data measured by the electroencephalogram measurement section 11 and the oculomotor measurement section 12, the state-of-attention determination section 15 calculates an eye fixation related potential, and based on the calculated lambda response amplitude value of the eye fixation related potential and the determination criterion adjusted by the determination criterion adjustment section 14, determines a state of attention to driving. Hereinafter, with reference to FIG. 14 and FIG. 15, the procedure of processing by the state-of-attention determination section 15 will be described.

Figure 14:
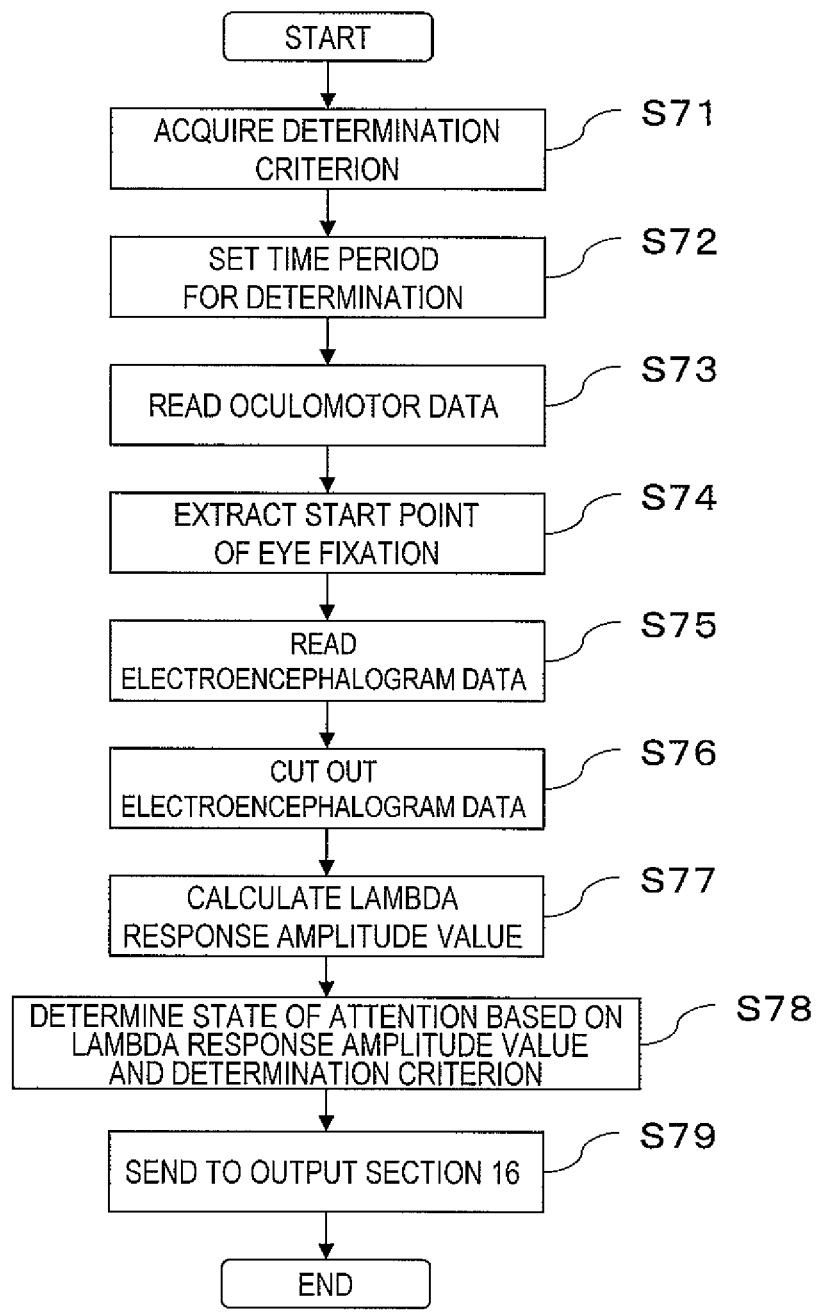
FIG. 14 is a flowchart showing a procedure of processing by a state-of-attention determination section 15.

FIG. 14 is a flowchart showing a procedure of processing by the state-of-attention determination section 15.

At step S71 in FIG. 14, the state-of-attention determination section 15 acquires the determination criterion having been adjusted by the determination criterion adjustment section 14, or more specifically, the optimum threshold of each driver.

At step S72, the state-of-attention determination section 15 decides a time period for determining the state of attention to driving. In advance, the state-of-attention determination section 15 retains data of time span TW (seconds) and time shift TS (seconds) for the time period for determination. The time span TW is a parameter that defines how long a zone the eye fixation related potential to be used should span, whereas the time shift TS is a parameter that defines every how many seconds the state of attention is to be calculated. For example, a time span of TW=20 seconds and a time shift of TS=5 seconds may be set.

However, the above setting values are exemplary. A short time span may be set within a range that conserves the accuracy of analysis, and the time shift amount is to be determined depending on the contemplated usage. For example, in the case where an immediate response is needed, e.g., alarming the driver as soon as possible when a low state of attention to driving is determined, a short time span TW=20 seconds/10 seconds/5 seconds and a short time shift TS=5 seconds may be set. On the other hand, in the case where accurate evaluations of states are needed when examining driver's state of attention after finishing driving, rather than providing immediate response, a relatively long time span TW=2 minutes or 3 minutes may be set.

Figure 15:
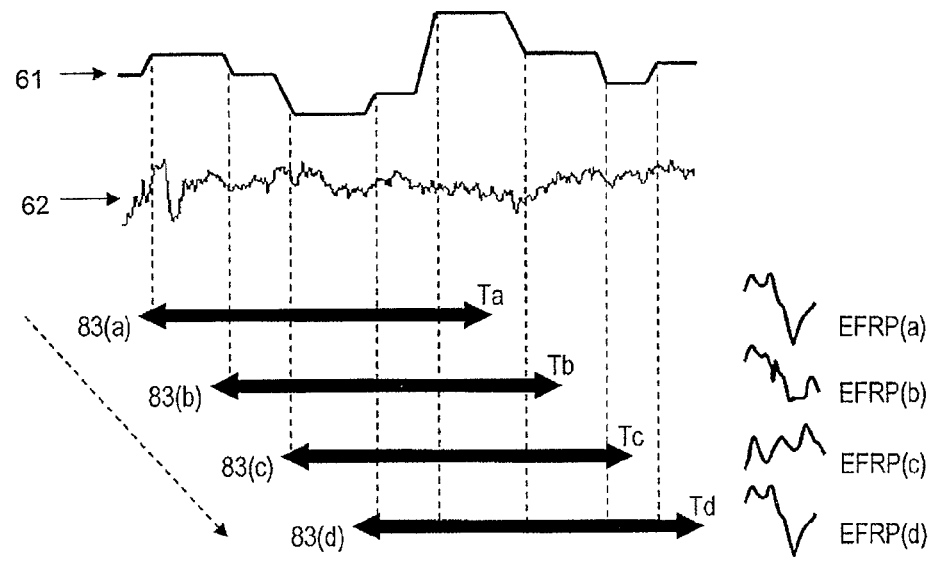
FIG. 15 is a diagram showing examples of time periods 83(a) to (d) for determination.

FIG. 15 shows examples of time periods 83(a) to (d) for determination. The time period for determination is a range of TW (seconds) back from the current time Ta; and when this step S72 is to be again executed TS (seconds) later, the time period for determination is a range of TW (seconds) back from the current time Tb(=Ta+TS). By thus moving the time period for determination in accordance with the lapse of time, the state of attention to driving of each moment can be determined.

The processes from step S73 to step S77 are identical to step S52 to step S56 described with reference to FIG. 12 and FIG. 13, and their specific descriptions are omitted.

At step S78, based on the lambda response amplitude value (L) calculated at step S77 and the threshold of each driver received at step S71, the state-of-attention determination section 15 determines the driver's state of attention to driving.

For example, in the case of determining whether the driver's state of attention corresponds to high or low, given the threshold Th, a "low" state of attention (i.e., a state of distraction) is determined if $L<Th$, or a "high" state of attention (i.e., a state of focused driving) is determined if $Th \leq L$. In the case of determining whether the driver's state of attention corresponds to high, medium, or low, two thresholds Th1 and Th2 (Th1<Th2) are received from the determination criterion adjustment section 14, and a "low" state of attention is determined if $L<Th1$, a "medium" state of attention is determined if $Th1 \leq L < Th2$, or a "high" state of attention is determined if $Th2 \leq L$.

At step S79, the state-of-attention determination section 15 sends the result of determination at step S7 to the output section 16.

Moreover, the state-of-attention determination section 15 causes the aforementioned series of processes to be repeated every time shift TS (seconds).

The output section 16 presents the result of determination by the state-of-attention determination section 15 in the form of an image or audio. If the state-of-attention determination section 15 determines a "low" state of attention, the output section 16 acts toward the driver so as to call the driver's attention. In other words, via action of the output section 16, the driver enjoys an assistance of inducing a change in state.

The method of outputting by the output section 16 to the driver may be calling out to the driver in audio form, presenting an operating sound or an alarm sound, or presenting text or an image on a car navigation system or a head-up display (HUD).

Figure 16:
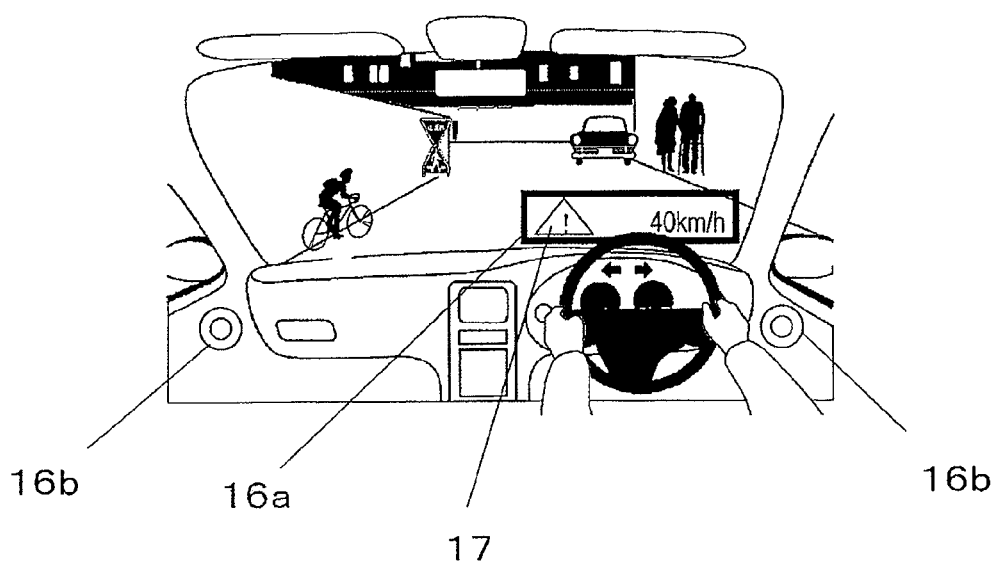
FIG. 16 is a diagram showing a specific example of an output section 16.

FIG. 16 shows an exemplary construction of the output section 16. On a head-up display 16a of the automobile, an image 17 for calling the attention of the driver is flickering. From a loudspeaker 16b in the car, an audio calling out to the driver is output. The attention calling to the driver may be done via both an image and an audio at the same time, or via only one of an image or an audio.

Otherwise, various methods that act on the perception of the driver may be adopted, e.g., direct presentation of information using an AR (Augmented Reality) technique of displaying an image in the form of an overlay on an object which needs attention, attention calling through a vibration of the steering wheel or the like, and an indirect intervention through a smell or adjustment of an amount of fanned air.

As the respective constituent elements of the state-of-attention determination apparatus 1 perform the above-described operations, the state-of-attention determination apparatus 1 executes the processes shown in FIG. 12 and FIG. 14. Thus, without each operator previously performing an explicit calibration task, the state-of-attention determination apparatus 1 can determine each operator's state of attention (e.g., a state of being focused on driving or a state of being distracted) with a high accuracy. As a result, based on the result of determination, an appropriate assistance such as attention calling can be provided for each operator.

Furthermore, advantages obtained by the present embodiment will be specifically described based on the results of trial calculations of distinction rates of the state of attention to driving.

The trial calculations of the distinction rate utilized the aforementioned experimental results. Herein, a "distinction rate" means a distinction rate between the two states of the state of focused driving and the state of distraction. With a time span of TW=180 seconds and a time shift of TS=30 seconds, an average value between the probability of correctly determining focused driving from the lambda response amplitude value under the driving-focused condition (0-Back test) and the probability of correctly determining distractedness from the lambda response amplitude value under the distracted condition (2-Back test) is defined as the aforementioned distinction rate.

FIGS. 17(a) to (d) show an average value among a total of 12 test subjects of the distinction rate of states of attention to driving determined under each of four conditions. The four conditions mean the distinction rate calculation being performed by using four different values, that is: (a) a threshold common to all test subjects; (b) an optimum threshold (estimated value) which is determined for each test subject from the lambda response amplitude value in a driving operation standby state according to the present invention; (c) an optimum threshold (estimated value) which is determined for each test subject from the lambda response amplitude value and an average power spectrum value of α waves, β waves, and θ waves in a driving operation standby state according to the present invention; and (d) an optimum threshold of each test subject as determined from both experimental results of focused driving and distractedness (corresponding to a previous explicit calibration task). The threshold common to all test subjects under condition (a) was an average value of the lambda response amplitudes under the respective conditions in the arithmetic mean waveform of all test subjects shown in FIG. 1A. Condition (d) means a condition where the driver was asked to previously perform an explicit calibration task.

Figure 17:
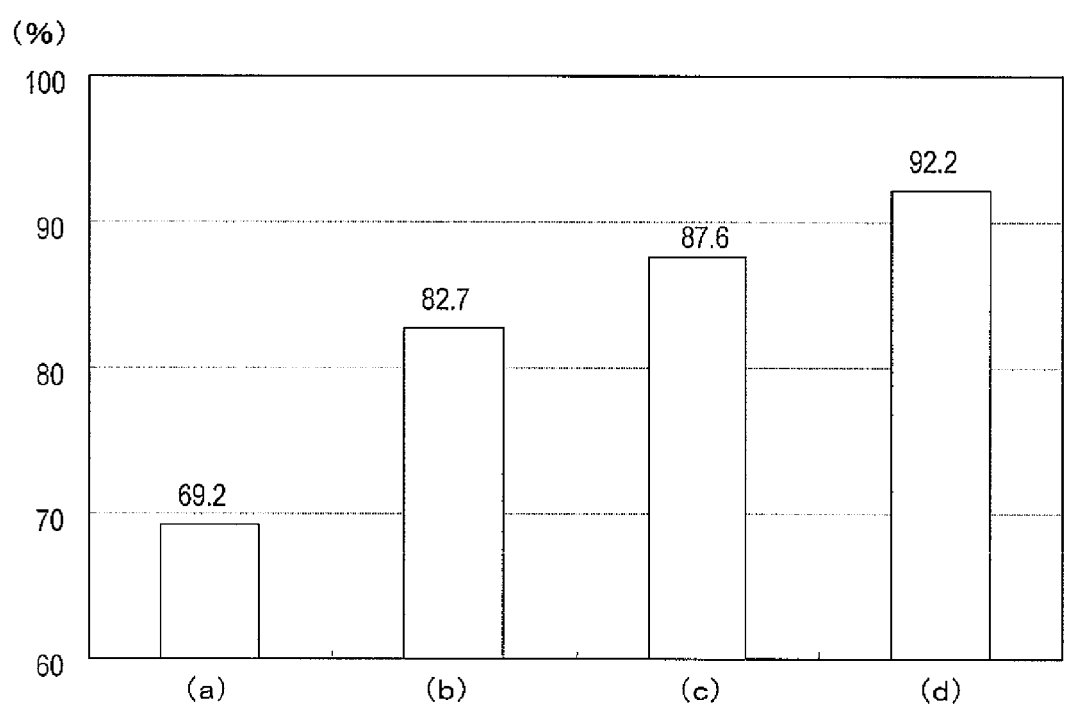
FIGS. 17(a) to 17(d) are diagrams showing average values, which are respectively derived under four conditions, of distinction rates of the state of attention to driving concerning all of 12 test subjects.

As shown in FIG. 17, the distinction rate is the lowest in case (a) of using a threshold which is common to all test subjects (69.2%), and the distinction rate is the highest in case (d) of using the optimum threshold of each test subject that is determined from a previous explicit calibration task (92.2%). On the other hand, the distinction rates in cases (b) and (c) of employing the present invention are 82.7% and 87.6%, respectively. Thus, it can be seen that determination is achieved with accuracies close to that of case (d), although no previous calibration task is performed.

The results shown in FIG. 17 indicate that a high accuracy of determination as to states of attention can be maintained according to the construction of the present embodiment, without asking the driver to previously perform a calibration task.

With the construction and procedure of processing according to the present embodiment, in a state-of-attention determination apparatus for determining a driver's state of attention, an optimum threshold for determining each driver's state of attention is calculated based on the lambda response amplitude value and power spectrum values of α waves, β waves, and θ waves in a driving operation standby state. As a result, without asking the driver to previously perform a calibration task, a high accuracy of determination as to states of attention can be maintained, and based on the result of determination, assistance of prompting a change in state, e.g., attention calling, can be appropriately provided for the driver.

The state-of-attention determination apparatus of the present embodiment has been illustrated as being integrally composed of a plurality of constituent elements. However, for example, some or all functions of the determination processing section 20 may be provided at separate positions from the electroencephalogram measurement section 11, the oculomotor measurement section 12, and the output section 16. For example, the determination processing section 20 may be realized by a computer in a remote place that is connected to the electroencephalogram measurement section 11 and the like via a wireless network. In this case, the determination processing section 20 itself functions as a state-of-attention determination apparatus. The electroencephalogram measurement section 11, the oculomotor measurement section 12, and the output section 16 are respectively realized as an electroencephalograph, an oculomotor measurement device as shown in FIG. 8, and a loudspeaker and a head-up display as shown in FIG. 16, that are separate from the state-of-attention determination apparatus.

The present specification illustrates a case where the state-of-attention determination apparatus 1 includes the output section 16. However, provision of the output section 16 is not essential. For example, the output section may be omitted and the result of determination may not be output, but rather stored to an internal memory (not shown) in the state-of-attention determination section 15. Alternatively, a recording device (e.g., a hard disk drive) for storing the results of determination and the determination threshold of states of attention may be provided inside the state-of-attention determination apparatus 1.

It has been illustrated that the state-of-attention determination apparatus of the present embodiment determines a state of focused driving when an amplitude value of the lambda response is equal to or greater than a threshold, and determines a state of distraction when it is smaller than the threshold. However, it may determine a state of distraction when the amplitude value of the lambda response is equal to the threshold.

The state-of-attention determination apparatus of the present embodiment has been illustrated as being used for the determination of states of attention during automobile driving. However, such usage is only exemplary, and automobile driving is not a limitation. A state-of-attention determination apparatus may be used in various situations where an operator performs operations of a device or the like. For example, it is applicable to the determination of the state of attention of an operator in a surveillance system, e.g., a control tower, plant facilities, and road monitoring. For example, the standby state existing before an operator performs a monitoring task may be defined to be from the timing with which the operator enters the monitoring room or logs into the surveillance system until the lapse of a predetermined time, whereby the state of attention of the operator can be accurately determined and appropriate monitoring work can be performed.

The present invention is applicable to any situation where there is a need to estimate how much attention is being allocated to the primary task of driving, operation, etc., not only to a driver of a common vehicle, but also to a driver driving a vehicle for business uses, e.g., a truck, a taxi, or a bus driver, or an operator of anything but a car, e.g., a train, an airplane, or a marine vessel, a plant supervisor of a factory or the like.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A state-of-attention determination apparatus comprising:
   an electroencephalograph configured to measure an electroencephalogram signal of an operator;
   an electrooculograph configured to measure an oculomotor signal indicating an oculomotor movement of the operator;
   a processor configured to:
      detect a time period during which the operator is making preparations prior to beginning a driving operation by receiving information concerning a start of a setting manipulation for a car navigation system provided in a vehicle, detecting a setting manipulation for the car navigation system, and determining the time period based on a time of the setting manipulation for the car navigation system;

adjust a determination criterion for determining a state of attention while the operator is performing a driving operation by extracting a portion of the electroencephalogram signal during the time period, obtaining a portion of the oculomotor signal during the time period to determine a first eye fixation, acquiring a first eye fixation related potential within the extracted portion of electroencephalogram signal by using the obtained first eye fixation, and adjusting the determination criterion based on the first eye fixation related potential; and extract a portion of the electroencephalogram signal measured after the time period, obtain a portion of the oculomotor signal measured after the time period to determine a second eye fixation, acquire a second eye fixation related potential from the portion of the electroencephalogram signal and the second eye fixation measured after the operator begins a driving operation, and determine a state of attention of the operator performing the driving operation based on the second eye fixation related potential and the adjusted determination criterion; and an output processor configured to output at least one of a visual, audio, vibration, or air indicator to call attention of the operator based on a result of the state of attention determination.

2. The state-of-attention determination apparatus of claim 1, wherein processor adjusts the determination criterion further based on a frequency power spectrum value of the electroencephalogram signal measured in the time period.

3. The state-of-attention determination apparatus of claim 2, wherein the processor sets a higher determination criterion as the power spectrum value of α waves contained in the electroencephalogram signal measured in the time period increases, and sets a lower determination criterion as the power spectrum value of β waves contained in the electroencephalogram signal measured in the time period increases.

4. The state-of-attention determination apparatus of claim 1, wherein the processor determines the state of attention of the operator by comparing an amplitude value of a lambda response of an arithmetic-mean of the second eye fixation related potential against a determination threshold which is the determination criterion.

5. The state-of-attention determination apparatus of claim 4, wherein, as the determination criterion, the processor sets a higher determination threshold as the lambda response amplitude value of the second eye fixation related potential increases, and sets a lower determination threshold as the lambda response amplitude value decreases.

6. The state-of-attention determination apparatus of claim 4, wherein, based on the oculomotor signal, the processor detects a start time of the eye fixation for either the first or second eye fixation related potentials to be a point in time at which the oculomotor movement of the operator has become smaller than a predetermined threshold.

7. The state-of-attention determination apparatus of claim 4, wherein the processor acquires the first and second eye fixation related potentials which is 50±100 milliseconds from a start time of the eye fixation in the electroencephalogram signal.

8. The state-of-attention determination apparatus of claim 4, wherein, as the amplitude value of the lambda response, the processor utilizes a local maximum contained within 50±100 milliseconds of the arithmetic-mean of the second eye fixation related potential based on an eye fixation start time as a starting point.

9. The state-of-attention determination apparatus of claim 1, wherein the processor determines that the operator is in a state of being focused on driving when an amplitude value of a lambda response of an arithmetic-mean of the second eye fixation related potential is equal to or greater than a determination threshold which is the determination criterion, and determines that the operator is in a state of being distracted when an amplitude value of a lambda response of the arithmetic-meaned eye fixation related potential is smaller than the determination threshold which is the determination criterion.

10. The state-of-attention determination apparatus of claim 1, wherein the processor detects the time period by defining as an end time at least one of the flowing points in time: completion of a setting manipulation for the car navigation system, detection of a vehicle speed of the vehicle being equal to or greater than a predetermined value, and a predetermined time after a start time.

11. The state-of-attention determination apparatus of claim 1, wherein, based on the oculomotor signal, the processor detects a start time of the eye fixation for either the first or second eye fixation related potentials to be a point in time at which the oculomotor movement of the operator has become smaller than a predetermined threshold.

12. The state-of-attention determination apparatus of claim 1, wherein the processor acquires the first and second eye fixation related potentials which is 50±100 milliseconds from a start time of the eye fixation in the electroencephalogram signal.

13. A state-of-attention determination apparatus comprising:

an electroencephalograph configured to measure an electroencephalogram signal of an operator;

an electrooculograph configured to measure an oculomotor signal indicating an oculomotor movement of the operator;

a processor configured to:

detect a time period during which the operator is making preparations prior to beginning a driving operation by receiving information concerning a release of a brake of a vehicle, detecting a release of the brake, and determining the time period based on a time of the release of the brake;

adjust a determination criterion for determining a state of attention while the operator is performing a driving operation by extracting a portion of the electroencephalogram signal during the time period, obtaining a portion of the oculomotor signal during the time period to determine a first eye fixation, acquiring a first eye fixation related potential within the extracted portion of electroencephalogram signal by using the obtained first eye fixation, and adjusting the determination criterion based on the first eye fixation related potential; and extract a portion of the electroencephalogram signal measured after the time period, obtain a portion of the oculomotor signal measured after the time period to determine a second eye fixation, acquire a second eye fixation related potential from the portion of the electroencephalogram signal and the second eye fixation measured after the operator begins a driving operation, and determine a state of attention of the operator performing the driving operation based on the second eye fixation related potential and the adjusted determination criterion; and an output processor configured to output at least one of a visual, audio, vibration, or air indicator to call attention of the operator based on a result of the state of attention determination.

\* \* \* \* \*